US007468435B2

(12) United States Patent
Waterhouse et al.

(10) Patent No.: US 7,468,435 B2
(45) Date of Patent: Dec. 23, 2008

(54) POLYDIAZENIUMDIOLATED CYCLIC POLYAMINES WITH POLYPHASIC NITRIC OXIDE RELEASE AND RELATED COMPOUNDS, COMPOSITIONS COMPRISING SAME AND METHODS OF USING SAME

(75) Inventors: David J. Waterhouse, Hillsborough, NJ (US); Preeya Kapur, Frederick, MD (US); Larry K. Keefer, Bethesda, MD (US); Joseph A. Hrabie, Frederick, MD (US); Frank De Rosa, Frederick, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 393 days.

(21) Appl. No.: 10/982,576

(22) Filed: Nov. 5, 2004

(65) Prior Publication Data

US 2005/0148566 A1 Jul. 7, 2005

Related U.S. Application Data

(63) Continuation-in-part of application No. PCT/US03/14180, filed on May 7, 2003.

(60) Provisional application No. 60/378,495, filed on May 7, 2002.

(51) Int. Cl.
 *C07D 245/00* (2006.01)
(52) U.S. Cl. ..................................... 540/470
(58) Field of Classification Search .............. None
 See application file for complete search history.

(56) References Cited

U.S. PATENT DOCUMENTS

| 5,155,137 | A | 10/1992 | Keefer et al. |
| 5,250,550 | A | 10/1993 | Keefer et al. |
| 5,366,997 | A | 11/1994 | Keefer et al. |
| 5,587,451 | A | 12/1996 | Athey et al. |
| 5,650,447 | A | 7/1997 | Keefer et al. |
| 5,721,365 | A | 2/1998 | Keefer et al. |
| 5,731,305 | A | 3/1998 | Keefer et al. |
| 5,910,316 | A | 6/1999 | Keefer et al. |
| 2005/0148566 | A1 * | 7/2005 | Waterhouse et al. ........ 514/183 |

FOREIGN PATENT DOCUMENTS

| WO | WO 98/13358 A1 | 4/1998 |
| WO | WO 01/92215 A2 | 12/2001 |

OTHER PUBLICATIONS

Wayland et al. Journal of the Chemical Society, Chemical Communications, 1976, 24, 1015-1016.*

Tamara et al. Tanpakushitsu Kakusan Koso, Bessatsu, 1976, 76(5), 225-40. (based on HCAPlus record).*

Atkins et al., "Macrocyclic Polyamines: 1,4,7,10,13,16-Hexaäzacyclooöctadecane" *Organic Synthesis*, Collective vol. VI, 652-661 (1988).

Barefield et al., "Synthesis of Macrocyclic Tetramines by Metal Ion Assisted Cyclization Reactions" *Inorg. Chem.*, 15 (6), 1370-1377 (1976).

Bellouard et al., "*cis*-Diprotected Cyclams and Cyclens: a New Route to Symmetrically or Asymmetrically 1,4-Disubstituted Tetraazamacrocycles and to Asymmetrically Tetrasubstituted Derivatives" *J. Chem. Soc., Perkin Trans*. 1, 3499-3505 (1999).

Boldrini et al., "Expeditious N-Monoalkylation of 1,4,7,10-Tetraazacyclododecane (cyclen)via Formamido Protection" *Tetrahedron Letters*, 41, 6527-6530 (2000).

Drago et al., "The Reaction of Nitrogen(II) Oxide with Various Primary and Secondary Amines" *J. Am. Chem. Soc.*, 83, 1819-1822 (Apr. 20, 1961).

Hrabie et al., "New Nitric Oxide-Releasing Zwitterions Derived from Polyamines" *J. Org. Chem.*, 58, 1472-1476 (1993).

Hrabie et al., "Adducts of Piperazine with Nitric Oxide" *Org. Prep. and Proc. Int.*, 31 (2), 189-192 (1999).

Kovacs et al., "pH Controlled Selective Protection of Polyaza Macrocycles" *Synthesis*, 759-763 (Jul. 1997).

Longhi et al., "Reactions of Nitrogen (II) Oxide with Miscellaneous Lewis Bases" *Inorg. Chem.*, 1 (4). 768-770 (Nov. 1962).

Meunier et al., "Synthesis and Characterization of Various Unsubstituted and Mono-N-Substituted Tetraazamacrocycles" *Can. J. Chem.*, 73, 685-695 (1995).

Militsopoulou et al., "Simple Synthesis of Cyclic Polyamines Using Selectively N-Tritylated Polyamines and Succinic Anhydride" *Tetrahedron Letters*, 43, 2593-2596 (2002).

(Continued)

*Primary Examiner*—James O. Wilson
*Assistant Examiner*—Noble Jarrell
(74) *Attorney, Agent, or Firm*—Leydig, Voit & Mayer, Ltd.

(57) ABSTRACT

The present invention provides compound of the formula (I):

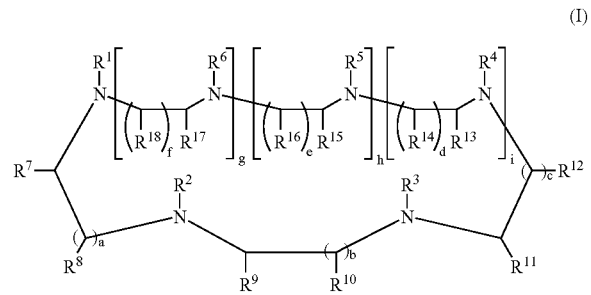

in which at least two of $R^1$, $R^2$, $R^3$, $R^4$, $R^5$, and $R^6$ are $N_2O_2M$ and related compounds substrates, compositions, and methods of using such compounds and compositions to treat biological disorders in which a polyphasic release of nitric oxide would be beneficial.

17 Claims, No Drawings

OTHER PUBLICATIONS

Panetta et al., "Triflamides for Protection and Cyclization of Tetraamines to Tetraazamacrocycles" *Tetrahedron Letters*, 33 (38), 5505-5508 (1992).

Reed et al., *Organic Synthesis*, 78, 73-81 (2000).

Yang et al., "Facile N-1 Protection of Cyclam, Cyclen and 1,4,7-Triazacyclononane" *Tetrahedron Letters*, 44, 2481-2483 (2003).

* cited by examiner

POLYDIAZENIUMDIOLATED CYCLIC POLYAMINES WITH POLYPHASIC NITRIC OXIDE RELEASE AND RELATED COMPOUNDS, COMPOSITIONS COMPRISING SAME AND METHODS OF USING SAME

CROSS-REFERENCE TO RELATED PATENT APPLICATIONS

This application claims priority to International Patent Application PCT/US03/14180, filed May 7, 2003, which claims the benefit of U.S. Provisional Patent Application No. 60/378,495, filed May 7, 2002.

FIELD OF THE INVENTION

This invention pertains to polydiazeniumdiolated cyclic polyamines with a polyphasic release of nitric oxide, related diazeniumdiolated compounds, compositions comprising same, and methods of using same.

BACKGROUND OF THE INVENTION

Nitric oxide (NO) is a simple diatomic molecule that plays a diverse and complex role in cellular physiology. It is known that NO is a powerful signaling compound and cytotoxic/cytostatic agent found in nearly every tissue of the human body, including endothelial cells, neural cells, and macrophages. NO has been implicated recently in a variety of bioregulatory processes, including normal physiological control of blood pressure, angiogenesis, and thrombosis, as well as neurotransmission, cancer, and infectious diseases. See, e.g., Moncada, "Nitric Oxide," *J. Hypertens. Suppl.* 12(10): S35-39 (1994); Moncada et al., "Nitric Oxide from L-Arginine: A Bioregulatory System," *Excerpta Medica*, International Congress Series 897 (Elsevier Science Publishers B.V.: Amsterdam, 1990); Marletta et al., "Unraveling the Biological Significance of Nitric Oxide," *Biofactors* 2: 219-225 (1990); Ignarro, "Nitric Oxide. A Novel Signal Transduction Mechanism for Transcellular Communication," *Hypertension* 16: 477-483 (1990); Hariawala et al., "Angiogenesis and the Heart: Therapeutic Implications," *J.R. Soc. Med.* 90(6): 307-311 (1997); Granger et al., "Molecular and Cellular Basis of Myocardial Angiogenesis," *Cell. Mol. Biol. Res.* 40(2): 81-85 (1994); Chiueh, "Neuroprotective Properties of Nitric Oxide," *Ann. N.Y. Acad. Sci.* 890: 301-311 (1999); Wink et al., "The Role of Nitric Oxide Chemistry in Cancer Treatment," *Biochemistry (Moscow)* 63(7): 802-809 (1998); Fang, F. C., "Perspectives Series: Host/Pathogen Interactions. Mechanisms of Nitric Oxide-Antimicrobial Activity," *J. Clin. Invest.* 99(12): 2818-25 (1997); and Fang, F. C., "Nitric Oxide and Infection," (Kluwer Academic/Plenum Publishers: New York, 1999).

Glyceryl trinitrate and sodium nitroprusside are two examples of vasodilators that currently enjoy widespread clinical use and whose pharmacological actions result from their metabolic conversion in situ to NO-releasing species. See, e.g., Ignarro et al., *J. Pharmocol. Exp. Ther.* 218: 739-749 (1981); Ignarro, *Annu. Rev. Pharmacol. Toxicol.* 30: 535-560 (1990); and Kruszyna et al., *Chem. Res. Toxicol.* 3: 71-76 (1990). In addition, other agents have been described in the literature which release NO spontaneously or following metabolic conversion of their parent or prodrug forms. See, e.g., Drago, *ACS Adv. Chem. Ser.* 36: 143-149 (1962); Longhi and Drago, *Inorg. Chem.* 2: 85 (1963); Schönafinger, "Heterocyclic NO prodrugs," *Farmaco* 54(5): 316-320 (1999); Hou et al., "Current trends in the Development of Nitric Oxide Donors," *Curr. Pharm. Des.* 5(6): 417-441 (1999); Muscara et al., "Nitric Oxide. V. Therapeutic Potential of Nitric Oxide Donors and Inhibitors," *Am. J. Physiol.* 276(6, Pt. 1): G1313-1316 (1999); Maragos et al., "Complexes of NO with Nucleophiles as Agents for the Controlled Biological Release of Nitric Oxide. Vasorelaxant Effects," *J. Med. Chem.* 34: 3242-3247 (1991); Fitzhugh et al., "Diazeniumdiolates: pro- and antioxidant applications of the 'NONOates,'" *Free Radic. Biol. Med.* 28(10): 1463-1469 (2000); Saavedra et al., "Diazeniumdiolates (Formerly NONOates) in Cardiovascular Research and Potential Clinical Applications," Nitric Oxide and the Cardiovascular System (Humana Press: Totowa, N.J., 2000); and Yamamoto et al., "Nitric oxide donors," *Proc. Soc. Exp. Biol. Med.* 225(3): 200-206 (2000).

NO-donor compounds can exert powerful tumoricidal and cytostatic effects. Such effects are attributable to NO's ability to inhibit mitochondrial respiration and DNA synthesis in certain cell lines. In addition to these bioregulatory properties, NO may arrest cell migration. These effects are apparently not limited to NO-donor compounds as macrophages can also sustain high levels of endogenous NO production via enzymatic mechanisms. Similar inhibitory effects have also been observed in other cells. See, e.g., Hibbs et al., "Nitric Oxide: A Cytotoxic Activated Macrophage Effector Molecule," *Biochem. and Biophys. Res. Comm.* 157: 87-94 (1988); Stuehr et al., "Nitric Oxide. A Macrophage Product Responsible for Cytostasis and Respiratory Inhibition in Tumor Target Cells," *J. Exp. Med.* 169: 1543-1555 (1989); Zingarelli, et al., "Oxidation, Tyrosine Nitration and Cytostasis Induction in the Absence of Inducible Nitric Oxide Synthase," *Int. J. Mol. Med.* 1(5): 787-795 (1998); Yamashita et al., "Nitric Oxide is an Effector Molecule in Inhibition of Tumor Cell Growth by rIFN-gamma-activated Rat Neutrophils," *Int. J. Cancer* 71(2): 223-230 (1997); Garg et al., "Nitric oxide-Generating Vasodilators Inhibit Mitogenesis and Proliferation of BALB/C 3T3 Fibroblasts by a Cyclic GMP-Independent Mechanisms," *Biochem. Biophys. Res. Commun.* 171: 474-479 (1990); and Sarkar et al., "Nitric Oxide Reversibly Inhibits the Migration of Cultured Vascular Smooth Muscle Cells," *Circ. Res.* 78(2): 225-30 (1996).

Medical research is rapidly discovering a number of potential therapeutic applications for NO-releasing compounds/materials, particularly in the fields of vascular surgery and interventional cardiology. For example, fatty deposits may build up on the wall of an artery as plaque. Over time as additional material is added, the plaque thickens, dramatically narrowing the cross-sectional area of the vessel lumen in a process known as arteriosclerosis. Blood flow to the heart muscle is compromised resulting in symptoms ranging from intermittent chest pain to easy fatigability. In an effort to reduce such symptoms and improve blood flow, patients with this condition may opt to undergo a procedure known as coronary artery bypass grafting (CABG). In a typical CABG procedure, a portion of a vein is removed from the leg. Sections of the vein are then used to bypass the site(s) of plaque-induced coronary artery narrowing. CABG involves a major surgical procedure wherein the patient's chest is opened to facilitate the operation; as a result, it carries with it appreciable morbidity and mortality risks. However, bypassing the site(s) of greatest narrowing with a grafted vein substantially alleviates the chest pain and fatigue that are common in this condition while reducing the risk of acute arterial blockage. A less invasive and increasingly common procedure for treating plaque-narrowed coronary arteries is called percutaneous transluminal coronary angioplasty (PTCA) (also known as balloon angioplasty). In PTCA, a catheter is inserted into the femoral artery of the patient's leg and threaded through the circulatory system until the site of coronary vessel occlusion is reached. Once at the site, a balloon on the tip of the catheter is inflated which compresses the plaque against the wall of the vessel. The balloon is then deflated and the catheter removed. PTCA results in dramatic improvement in coronary blood flow as the cross-sectional area of the vessel lumen is increased substantially by this procedure. However, complications of this procedure may include thrombus formation at the site of PTCA-treatment, vessel rupture from overextension, or complete collapse of the vessel immediately following deflation of the balloon. These complications can lead to significant alterations in blood flow with resultant damage to the heart muscle.

A more general complication of angioplasty is restenosis, a complex multi-factorial process that is initiated when thrombocytes (platelets) migrate to the injury site and release mitogens into the injured endothelium. Clot formation or thrombogenesis occurs as activated thrombocytes and fibrin begin to aggregate and adhere to the compressed plaque on the vessel wall. Mitogen secretion also causes the layers of vascular smooth muscle cells below the site of injury (neointima) to over proliferate, resulting in an appreciable thickening of the injured vessel wall. Within six months of PTCA-treatment roughly 30 to 50% of patients exhibit significant or complete re-occlusion of the vessel.

Nitric oxide has recently been shown to dramatically reduce thrombocyte and fibrin aggregation/adhesion and smooth muscle cell hyperplasia while promoting endothelial cell growth (Cha et al., "Effects of Endothelial Cells and Mononuclear Leukocytes on Platelet Aggregation," *Haematologia (Budap)* 30(2): 97-106 (2000); Lowson et al., "The Effect of Nitric Oxide on Platelets When Delivered to the Cardiopulmonary Bypass Circuit," *Anest. Analg.* 89(6): 1360-1365 (1999); Riddel et al., "Nitric Oxide and Platelet Aggregation," *Vitam. Horm.* 57: 25-48 (1999); Gries et al., "Inhaled Nitric Oxide Inhibits Human Platelet Aggregation, P-selectin expression, and Fibrinogen Binding In Vitro and In Vivo," *Circulation* 97(15): 1481-1487 (1998); and Lüscher, "Thrombocyte-vascular Wall Interaction and Coronary Heart Disease," *Schweiz. 'Med. Wochenschr.* 121(51-52): 1913-1922 (1991)). NO is one of several "drugs" under development by researchers as a potential treatment for the restenotic effects associated with intracoronary stent deployment. However, because the cascade of events leading to irreparable vessel damage can occur within seconds to minutes of stent deployment, it is essential that any anti-restenotic "drug" therapy be available at the instant of stent implantation. Also, it is widely thought that such therapy may need to continue for some time afterwards as the risk of thrombogenesis and restenosis persists until an endothelial lining has been restored at the site of injury.

In theory, one approach for treating such complications involves prophylactically supplying the PTCA-injury site with therapeutic levels of NO. This can be accomplished by stimulating the endogenous production of NO or using exogenous NO sources. Methods to regulate endogenous NO release have primarily focused on activation of enzymatic pathways with excess NO metabolic precursors like L-arginine and/or increasing the local expression of nitric oxide synthase (NOS) using gene therapy. U.S. Pat. Nos. 5,945,452, 5,891,459, and 5,428,070 describe the sustained NO elevation using orally administered L-arginine and/or L-lysine while U.S. Pat. Nos. 5,268,465, 5,468,630, and 5,658,565 describe various gene therapy approaches. Other various gene therapy approaches have been described in the literature. See, e.g., Smith et al., "Gene Therapy for Restenosis," *Curr. Cardiol. Rep.* 2(1): 13-23 (2000); Alexander et al., "Gene Transfer of Endothelial Nitric Oxide Synthase but not Cu/Zn Superoxide Dismutase restores Nitric Oxide Availability in the SHRSP," *Cardiovasc. Res.* 47(3): 609-617 (2000); Channon et al., "Nitric Oxide Synthase in Atherosclerosis and Vascular Injury: Insights from Experimental Gene Therapy," *Arterioscler. Thromb. Vasc. Biol.* 20(8): 1873-1881 (2000); Tanner et al., "Nitric Oxide Modulates Expression of Cell Cycle Regulatory Proteins: A Cytostatic Strategy for Inhibition of Human Vascular Smooth Muscle Cell Proliferation," *Circulation* 101(16): 1982-1989 (2000); Kibbe et al., "Nitric Oxide Synthase Gene Therapy in Vascular Pathology," *Semin. Perinatol.* 24(1): 51-54 (2000); Kibbe et al., "Inducible Nitric Oxide Synthase and Vascular Injury," *Cardiovasc. Res.* 43(3): 650-657 (1999); Kibbe et al., "Nitric Oxide Synthase Gene Transfer to the Vessel Wall," *Curr. Opin. Nephrol. Hypertens.* 8(1): 75-81 (1999); Vassalli et al., "Gene Therapy for Arterial Thrombosis," *Cardiovasc. Res.* 35(3): 459-469 (1997); and Yla-Herttuala, "Vascular Gene Transfer," *Curr. Opin. Lipidol.* 8(2): 72-76 (1997). However, these methods have not proved clinically effective in preventing restenosis. Similarly, regulating endogenously expressed NO using gene therapy techniques such as NOS vectors remains highly experimental. Also, there remain significant technical hurdles and safety concerns that must be overcome before site-specific NOS gene delivery will become a viable treatment modality.

The exogenous administration of gaseous nitric oxide is not feasible due to the highly toxic, short-lived, and relatively insoluble nature of NO in physiological buffers. As a result, the clinical use of gaseous NO is largely restricted to the treatment of neonates with conditions such as persistent pulmonary hypertension (Weinberger et al., "The Toxicology of Inhaled Nitric Oxide," *Toxicol. Sci.* 59(1), 5-16 (2001); Kinsella et al., "Inhaled Nitric Oxide: Current and Future Uses in Neonates," *Semin. Perinatol.* 24(6), 387-395 (2000); and Markewitz et al., "Inhaled Nitric Oxide in Adults with the Acute Respiratory Distress Syndrome," *Respir. Med.* 94(11), 1023-1028 (2000)). Alternatively, however, the systemic delivery of exogenous NO with such prodrugs as nitroglycerin has long enjoyed widespread use in the medical management of angina pectoris or the "chest pain" associated with atherosclerotically narrowed coronary arteries. There are problems with the use of agents such as nitroglycerin. Because nitroglycerin requires a variety of enzymes and cofactors in order to release NO, repeated use of this agent over short intervals produces a diminishing therapeutic benefit. This phenomenon is called drug tolerance and results from the near or complete depletion of the enzymes/cofactors needed in the blood to efficiently convert nitroglycerin to a NO-releasing species. By contrast, if too much nitroglycerin is initially given to the patient, it can have devastating side effects including severe hypotension and free radical cell damage.

Because of problems associated with the systemic delivery of NO, there has been a recent shift towards identifying agents/materials capable of directly releasing NO or other antirestenotic agents over a prolonged period directly at the site of PTCA-vascular injury. As a result, there exists a substantial need for a stent comprised of or coated with a material capable of continuously releasing NO from the instant of contact with a blood field and subsequently releasing NO days or weeks following its deployment in a coronary artery. Such a device potentially represents an ideal means of treating the restenosis that frequently accompanies the implantation of a stent into a coronary artery. See, e.g., U.S. Pat. Nos. 6,087,479 and 5,650,447, U.S. Patent Application No. 2001/

0000039, and PCT No. WO 00/02501, that detail approaches to develop NO-releasing coatings for metallic stents and other medical devices.

Diazeniumdiolates, compounds containing the moiety

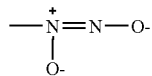

comprise a diverse class of NO-releasing compounds/materials that are known to exhibit sufficient stability to be useful as therapeutics. Although the N-bound diazeniumdiolates were first discovered by Reilly (U.S. Pat. No. 3,153,094) and Drago et al., *J. Am. Chem. Soc.* 82: 96-98 (1960) more than 40 years ago, the chemistry and properties of these diazeniumdiolates have been extensively reinvestigated by Keefer and co-workers, as described in U.S. Pat. Nos. 4,954,526, 5,039, 705, 5,155,137, 5,212,204, 5,250,550, 5,366,997, 5,405,919, 5,525,357, and 5,650,447, and in J. A. Hrabie et al., *J. Org. Chem.* 58: 1472-1476 (1993), and incorporated herein by reference.

Because many NO-releasing diazeniumdiolates have been prepared from amines, one potential approach for treating PTCA-associated restenosis is to coat the device with a suitably diazeniumdiolated amine-functionalized polymeric material. U.S. Pat. No. 5,405,919, for example, describes several biologically acceptable, amine-functionalized polyolefin-derived polymers. However, polyolefin-based coatings are prone to fractures as the coating is stressed during procedures such as stent expansion. Were such a fracture to occur, it might cause particulate fragments from the coating to be released into the lumen of the overstretched vessel, ultimately lodging downstream in much narrower arteriolae and capillaries and compromising blood flow to those portions of the heart muscle that are supplied by the affected artery. Additionally, polyolefin-based and -coated medical devices tend to be more prone to the development of biofilms and device-related infections. These problems suggest that polyolefin-based materials may not be appropriate for uses in which permanent in situ implantation is desired. By contrast, metallic medical devices have repeatedly been shown to exhibit bio- and hemocompatibility properties that are superior to many polyolefin-based materials. See, Palmaz, "Review of Polymeric Graft Materials for Endovascular Applications," *J. Vasc. Interv. Radiol.* 9(1 Pt. 1): 7-13 (1998); Tepe et al., "Covered Stents for Prevention of Restenosis. Experimental and Clinical Results with Different Stent Designs," *Invest. Radiol.* 31(4): 223-229 (1996); Fareed, "Current Trends in Antithrombotic Drug and Device Development," *Semin. Thromb. Hemost.* 22(Suppl. 1): 3-8 (1996); Bolz et al., "Coating of Cardiovascular Stents with a Semiconductor to Improve Their Hemocompatibility," *Tex. Heart Inst. J* 23(2): 162-166 (1996); De Scheerder et al., "Biocompatibility of Polymer-Coated Oversized Metallic Stents Implanted in Normal Porcine Coronary Arteries," *Atherosclerosis* 114(1): 105-114 (1995); and Libby et al., "Ultrasmooth Plastic to Prevent Stent Clogging," *Gastrointest. Endosc.* 40(3): 386-387 (1994). More recently, quite dramatic improvements in bio- and hemocompatibility have also been observed in medical devices coated with certain polymeric materials (e.g., silicone, hydrogel, heparin-, albumin-, phosphorylcholine-functionalized polymers and the like). See, e.g., Malik et al., "Phosphorylcholine-Coated Stents in Porcine Coronary Arteries. In Vivo Assessment of Biocompatibility," *J. Invasive Cardiol.* 13(3): 193-201 (2001); Tsang et al., "Silicone-Covered Metal Stents: An In Vitro Evaluation for Biofilm Formation and Patency," *Dig. Dis. Sci.* 44(9): 1780-1785 (1999); Kuiper et al., "Phosphorylcholine-coated Metallic Stents in Rabbit Illiac and Porcine Coronary Arteries," *Scand. Cardiovasc. J.* 32(5): 261-268 (1998); and McNair, "Using Hydrogel Polymers for Drug Delivery," *Med. Device Technol.* 7(10): 16-22 (1996).

When exposed to hydrogen ion (i.e., proton) donors such as, for example, water or physiological fluids, most diazeniumdiolates bearing unshielded and unprotected [(NO)NO]⁻ groups rapidly break down via clean first-order kinetic processes in which an initial surge of NO is followed by a steadily but diminishing (i.e., first-order) rate of release until the entire NO content of the material has been exhausted. For most diazeniumdiolated compounds, such processes are complete within minutes to a few hours of the initial NO burst.

Simple diazeniumdiolate ions have a characteristic absorbance maximum at or near 250 nm and are relatively stable under basic conditions. The amine/NO complexes release NO upon dissolution at physiological conditions, pH 7.4 and 37° C. Drago (Reactions of Nitrogen (II) Oxide. *ACS Advances in Chemistry Series.* 1962, 36, 143-149) described the reaction of nitric oxide with primary and secondary amines to form intermolecular salts, where one amine exists as a diazeniumdiolate with a negative charge and the other amine is protonated, giving it a positive charge. Hrabie et al. (New Nitric Oxide Releasing Zwitterions Derived from Polyamines. *J. Org. Chem.*, 1993, 58, 1472-1476) studied the reaction of polyamines with NO to form intramolecular salts, zwitterions, which exhibit varying release rates of NO from around 1.3 min to 20 hours depending on the structure of the attached polyamine. Other monodiazeniumdiolated (poly)amine compounds have been prepared (see, for example, U.S. Pat. Nos. 5,731,305, 5,250,550, and 5,155,137), but the NO release data only indicated a clean first order nitric oxide release.

It was believed that in order to treat a disorder with nitric oxide over a period of time, two compounds would have to be co-administered—one compound with a quick release of NO and a second compound with an NO release rate several times longer than the first compound. This route would require that both compounds be approved by the FDA, an expensive and time-consuming endeavor. Alternatively, the same compound could be administered multiple times in order to provide a lasting treatment. However, this method increases the cost of treatment because of increased dosing and subjects the patient to increased exposure to any potential side effects.

Hrabie et al. (Adducts of piperazine with Nitric Oxide. *Organic Preparations and Procedures International,* 1999, 31(2), 189-192 and U.S. Pat. No. 5,721,365) examined adducts of the cyclic polyamine piperazine with nitric oxide. The bisdiazeniumdiolate of piperazine was reported to have a biphasic release of NO with an initial half-life of 2.3 minutes and a secondary half-life of 5.0 minutes. In fact due to the similarity in the initial and secondary release rates for the bisdiazeniumdiolate of piperazine, it was initially believed that the two release rates were identical. Because the profile of the biphasic release of NO from the bisdiazeniumdiolate of piperazine was on such a similar time scale, and because the second half-life of NO release was only 5.0 minutes, such a compound is not practical to use for conditions requiring a release of NO greater than a five-minute half-life. In addition, the use of piperazine diazeniumdiolate in pharmaceutical compositions is not desirable because of the potential toxicity of its possible nitrosopiperazine metabolite.

Previous research also discloses polydiazeniumdiolated polymers. Such NO-releasing polymers can have multiple phases of NO release. However, NO-releasing polymers often have kinetics that are too difficult to control and/or reproduce. The polymer structure, ionophore concentration, plasticizer content, physical shape and size of polymer mass, conformation, and placement of $N_2O_2^-$ groups can affect how much and when the NO is released. Moreover, the administration of NO-releasing polymers can be hindered by poor solubility and lack of structural homogeneity.

Therefore, it would be beneficial to administer a single, physiologically acceptable compound having a polyphasic NO release profile, where the initial first order release or burst of NO is on a relatively short time scale (e.g., seconds to minutes) and the additional first order release(s) of NO is on a longer relative time scale (e.g., hours to days). A compound capable of polyphasic release of NO would enable an acute treatment (e.g., the initial burst of NO) and sustained treatment (e.g., additional phase releases of NO) of a disorder in which the patient would receive the maximum benefits of treatment with a minimal dosage. Administration of a single compound with polyphasic NO release would require FDA approval of only one compound and would decrease the dosages and any potential side effects. Such compounds would additionally be beneficial to provide medical devices, e.g., stents, in the prevention of restenosis after removal of an arterial blockage, that are used in conjunction with such compounds as a means for effective delivery of the compounds.

The invention provides for such a compound. These and other advantages of the invention, as well as additional inventive features, will be apparent from the description of the invention provided herein.

BRIEF SUMMARY OF THE INVENTION

The present invention provides a compound of the formula (I):

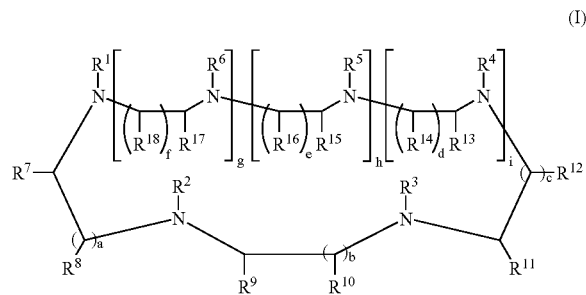

in which at least two of $R^1$, $R^2$, $R^3$, $R^4$, $R^5$, and $R^6$ are $N_2O_2M$, and the remaining $R^n$, i.e., $R^1$, $R^2$, $R^3$, $R^4$, $R^5$, and $R^6$, substituent(s) that are not $N_2O_2M$ can be the same or different and are independently selected from the group consisting of hydrogen, an unsubstituted or substituted $C_{1-12}$ straight chain alkyl, an unsubstituted or substituted $C_{3-12}$ branched chain alkyl, an unsubstituted or substituted $C_{3-12}$ straight chain alkenyl, an unsubstituted or substituted $C_{3-12}$ branched chain alkenyl, an unsubstituted or substituted aralkyl, an unsubstituted or substituted aryl, an unsubstituted or substituted acyl, an unsubstituted or substituted alkoxycarbonyl, an unsubstituted or substituted aryloxycarbonyl, carboxamido, an unsubstituted or substituted heteroaryl, sulfonyl, sulfinyl, sulfenyl, phosphoryl, phosphinyl, silyl, cyano, glycosyl, and a cyclic polyamine compound comprising 3 to 6 amino groups that is bound through either a carbon or nitrogen atom in the backbone of the compound;

$R^7$-$R^{18}$, i.e., $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$, can be the same or different and are independently selected from the group consisting of hydrogen, an unsubstituted or substituted $C_{1-12}$ straight chain alkyl, an unsubstituted or substituted $C_{3-12}$ branched chain alkyl, an unsubstituted or substituted $C_{2-12}$ straight chain alkenyl, an unsubstituted or substituted $C_{3-12}$ branched chain alkenyl, an unsubstituted or substituted alkoxy, an unsubstituted or substituted aralkyl, an unsubstituted or substituted aryl, an unsubstituted or substituted heteroaryl, an unsubstituted or substituted arylamino, an unsubstituted or substituted alkylamino, carboxyalkylamino, carboxydialkylamino, an unsubstituted or substituted acetoxy, an unsubstituted or substituted carboxyalkyl, an unsubstituted or substituted alkylcarbonyl, an unsubstituted or substituted alkylthio, an unsubstituted or substituted alkyloxy, carboxamido, an unsubstituted or substituted alkylcarboxamido, an unsubstituted or substituted dialkylcarboxamido, an unsubstituted or substituted phenoxy, an unsubstituted or substituted benzyloxy, phenylcarbonyl, benzylcarbonyl, silyl, and a cyclic polyamine compound comprising 3 to 6 amino groups that is bound through either a carbon or nitrogen atom in the backbone of the compound;

each M is the same or different and is a pharmaceutically acceptable cation (i.e., a noncovalently bound counterion);

a-f are integers independently from 1 to 3; and
g, h, and i are independently 0 or 1.

In one aspect, the invention provides a cyclic polyamine compound comprising at least three amino groups, wherein at least two of the amino groups are covalently bound to a nitrogen oxide-releasing group of the formula $N_2O_2M$, wherein M is a pharmaceutically acceptable cation. A compound that has a polyphasic release of nitric oxide, wherein an initial release of nitric oxide has a rate that is at least 3 times greater than any subsequent rate of nitric oxide release.

In another aspect, the invention provides substrates and compositions, including pharmaceutical compositions, comprising a cyclic polyamine diazeniumdiolate of the present invention that has a polyphasic release of NO.

In yet another aspect, the invention provides a pharmaceutical composition comprising a pharmaceutically acceptable carrier and a compound that releases at least one mole of nitric oxide within about 2 minutes under physiological conditions and at least one additional mole of nitric oxide beyond about 5 minutes under physiological conditions.

The present invention further provides a method for treating or preventing a biological disorder in a mammal in which a polyphasic release of nitric oxide is beneficial, comprising administering to the mammal a cyclic polyamine diazeniumdiolate of the present invention in an amount sufficient to treat or prevent the biological disorder.

DETAILED DESCRIPTION OF THE INVENTION

The invention provides a cyclic polyamine compound comprising at least three amino groups, in which at least two of the amino groups are covalently bound to a nitrogen oxide-releasing group of the formula $N_2O_2M$, wherein M is a pharmaceutically acceptable cation. The invention also provides a compound that has a polyphasic release of nitric oxide, wherein an initial release of nitric oxide has a rate that is at least about 3 times greater than any subsequent rate of nitric oxide release. Another aspect of the invention is a pharmaceutical composition comprising a pharmaceutically acceptable carrier and a compound that releases at least one mole (preferably at least two moles) of nitric oxide within about 2 minutes under physiological conditions and at least one additional mole (preferably at least two additional moles) of nitric oxide beyond about 5 minutes under physiological conditions.

The present invention provides a compound of the formula (I):

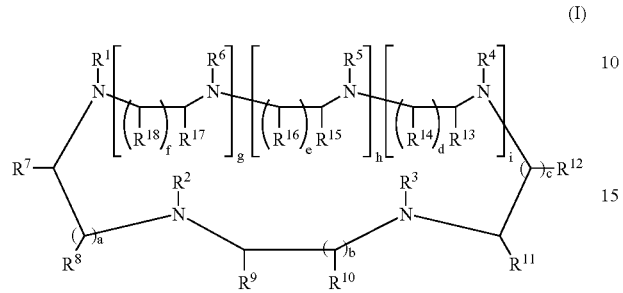

(I)

in which at least two of $R^1$, $R^2$, $R^3$, $R^4$, $R^5$, and $R^6$ are $N_2O_2M$, and the remaining R″, i.e., $R^1$, $R^2$, $R^3$, $R^4$, $R^5$, or $R^6$, substituent(s) that are not $N_2O_2M$ can be the same or different and are independently selected from the group consisting of hydrogen, an unsubstituted or substituted $C_{1-12}$ straight chain alkyl, an unsubstituted or substituted $C_{3-12}$ branched chain alkyl, an unsubstituted or substituted $C_{3-12}$ straight chain alkenyl, an unsubstituted or substituted $C_{3-12}$ branched chain alkenyl, an unsubstituted or substituted aralkyl, an unsubstituted or substituted aryl, an unsubstituted or substituted acyl, an unsubstituted or substituted alkoxycarbonyl, an unsubstituted or substituted aryloxycarbonyl, carboxamido, an unsubstituted or substituted heteroaryl, sulfonyl, sulfinyl, sulfenyl, phosphoryl, phosphinyl, silyl, cyano, glycosyl, and a cyclic polyamine compound comprising 3 to 6 amino groups that is bound through either a carbon or nitrogen atom in the backbone of the compound;

$R^7$-$R^{18}$, i.e., $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$, can be the same or different and are independently selected from the group consisting of hydrogen, an unsubstituted or substituted $C_{1-12}$ straight chain alkyl, an unsubstituted or substituted $C_{3-12}$ branched chain alkyl, an unsubstituted or substituted $C_{2-12}$ straight chain alkenyl, an unsubstituted or substituted $C_{3-12}$ branched chain alkenyl, an unsubstituted or substituted alkoxy, an unsubstituted or substituted aralkyl, an unsubstituted or substituted aryl, an unsubstituted or substituted heteroaryl, an unsubstituted or substituted arylamino, an unsubstituted or substituted alkylamino, carboxyalkylamino, carboxydialkylamino, an unsubstituted or substituted acetoxy, an unsubstituted or substituted carboxyalkyl, an unsubstituted or substituted alkylcarbonyl, an unsubstituted or substituted alkylthio, an unsubstituted or substituted alkyloxy, carboxamido, an unsubstituted or substituted alkylcarboxamido, an unsubstituted or substituted dialkylcarboxamido, an unsubstituted or substituted phenoxy, an unsubstituted or substituted benzyloxy, phenylcarbonyl, benzylcarbonyl, silyl, and a cyclic polyamine compound comprising 3 to 6 amino groups that is bound through either a carbon or nitrogen atom in the backbone of the compound;

each M can be the same or different and is a pharmaceutically acceptable cation;

a-f are integers independently from 1 to 3; and g, h, and i are independently 0 or 1.

Alternatively, two adjacent nitrogen $R^1$, $R^2$, $R^3$, $R^4$, $R^5$, and $R^6$ substituent(s) that are not $N_2O_2M$, together can form dione (—C(O)C(O)—).

In one embodiment of the invention provides a compound of the formula (II):

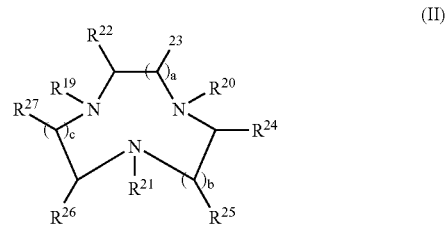

(II)

wherein at least two of $R^{19}$, $R^{20}$, and $R^{21}$ are $N_2O_2M$, and the remaining R″, i.e., $R^{19}$, $R^{20}$, and $R^{21}$ substituent that is not $N_2O_2M$ is selected from the group consisting of hydrogen, an unsubstituted or substituted $C_{1-12}$ straight chain alkyl, an unsubstituted or substituted $C_{3-12}$ branched chain alkyl, an unsubstituted or substituted $C_{3-12}$ straight chain alkenyl, an unsubstituted or substituted $C_{3-12}$ branched chain alkenyl, an unsubstituted or substituted aralkyl, an unsubstituted or substituted aryl, an unsubstituted or substituted acyl, an unsubstituted or substituted alkoxycarbonyl, an unsubstituted or substituted aryloxycarbonyl, carboxamido, an unsubstituted or substituted heteroaryl, sulfonyl, sulfinyl, sulfenyl, phosphoryl, phosphinyl, silyl, cyano, glycosyl, and a cyclic polyamine compound comprising 3 to 6 amino groups that is bound through either a carbon or nitrogen atom in the backbone of the compound;

$R^{23}$-$R^{27}$, i.e., $R^{23}$, $R^{24}$, $R^{25}$, $R^{26}$, and $R^{27}$, can be the same or different and are independently selected from the group consisting of hydrogen, an unsubstituted or substituted $C_{1-12}$ straight chain alkyl, an unsubstituted or substituted $C_{3-12}$ branched chain alkyl, an unsubstituted or substituted $C_{2-12}$ straight chain alkenyl, an unsubstituted or substituted $C_{3-12}$ branched chain alkenyl, an unsubstituted or substituted alkoxy, an unsubstituted or substituted aralkyl, an unsubstituted or substituted aryl, an unsubstituted or substituted heteroaryl, an unsubstituted or substituted arylamino, an unsubstituted or substituted alkylamino, carboxyalkylamino, carboxydialkylamino, an unsubstituted or substituted acetoxy, an unsubstituted or substituted carboxyalkyl, an unsubstituted or substituted alkylcarbonyl, an unsubstituted or substituted alkylthio, an unsubstituted or substituted alkyloxy, carboxamido, an unsubstituted or substituted alkylcarboxamido, an unsubstituted or substituted dialkylcarboxamido, an unsubstituted or substituted phenoxy, an unsubstituted or substituted benzyloxy, phenylcarbonyl, benzylcarbonyl, silyl, and a cyclic polyamine compound comprising 3 to 6 amino groups that is bound through either a carbon or nitrogen atom in the backbone of the compound;

each M can be the same or different and is a pharmaceutically acceptable cation; and a-c are integers independently from 1 to 3.

Alternatively, two adjacent nitrogen $R^{19}$, $R^{20}$, and $R^{21}$ substituent(s) (e.g., $R^{19}/R^{20}$, $R^{19}/R^{21}$, $R^{20}/R^{21}$) that are not $N_2O_2M$, together can form dione (—C(O)C(O)—).

Another embodiment of the present invention provides a compound of the formula (III):

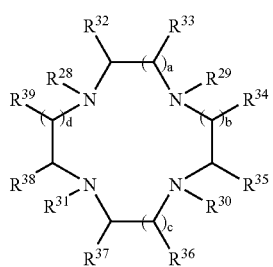

(III)

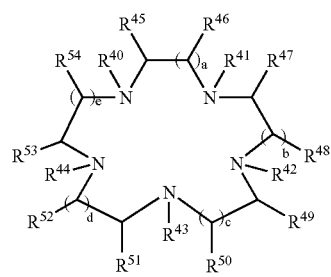

(IV)

wherein at least two of $R^{28}$, $R^{29}$, $R^{30}$, and $R^{31}$ are $N_2O_2M$, and the remaining R″, i.e., $R^{28}$, $R^{29}$, $R^{30}$, and $R^{31}$ substituent(s) that are not $N_2O_2M$ can be the same or different and are independently selected from the group consisting of hydrogen, an unsubstituted or substituted $C_{1-12}$ straight chain alkyl, an unsubstituted or substituted $C_{3-12}$ branched chain alkyl, an unsubstituted or substituted $C_{3-12}$ straight chain alkenyl, an unsubstituted or substituted $C_{3-12}$ branched chain alkenyl, an unsubstituted or substituted aralkyl, an unsubstituted or substituted aryl, an unsubstituted or substituted acyl, an unsubstituted or substituted alkoxycarbonyl, an unsubstituted or substituted aryloxycarbonyl, carboxamido, an unsubstituted or substituted heteroaryl, sulfonyl, sulfinyl, sulfenyl, phosphoryl, phosphinyl, silyl, cyano, glycosyl, and a cyclic polyamine compound comprising 3 to 6 amino groups that is bound through either a carbon or nitrogen atom in the backbone of the compound;

$R^{32}$-$R^{39}$, i.e., $R^{32}$, $R^{33}$, $R^{34}$, $R^{35}$, $R^{36}$, $R^{37}$, $R^{38}$, and $R^{39}$, can be the same or different and are independently selected from the group consisting of hydrogen, an unsubstituted or substituted $C_{1-12}$ straight chain alkyl, an unsubstituted or substituted $C_{3-12}$ branched chain alkyl, an unsubstituted or substituted $C_{2-12}$ straight chain alkenyl, an unsubstituted or substituted $C_{3-12}$ branched chain alkenyl, an unsubstituted or substituted alkoxy, an unsubstituted or substituted aralkyl, an unsubstituted or substituted aryl, an unsubstituted or substituted heteroaryl, an unsubstituted or substituted arylamino, an unsubstituted or substituted alkylamino, carboxyalkylamino, carboxydialkylamino, an unsubstituted or substituted acetoxy, an unsubstituted or substituted carboxyalkyl, an unsubstituted or substituted alkylcarbonyl, an unsubstituted or substituted alkylthio, an unsubstituted or substituted alkyloxy, carboxamido, an unsubstituted or substituted alkylcarboxamido, an unsubstituted or substituted dialkylcarboxamido, an unsubstituted or substituted phenoxy, an unsubstituted or substituted benzyloxy, phenylcarbonyl, benzylcarbonyl, silyl, and a cyclic polyamine compound comprising 3 to 6 amino groups that is bound through either a carbon or nitrogen atom in the backbone of the compound;

each M can be the same or different and is a pharmaceutically acceptable cation; and a-d are integers independently from 1 to 3.

Alternatively, two adjacent $R^{28}$, $R^{29}$, $R^{30}$, and $R^{31}$ substituent(s) (e.g., $R^{28}$/$R^{29}$, $R^{30}$/$R^{31}$, $R^{28}$/$R^{31}$, $R^{29}$/$R^{30}$) that are not $N_2O_2M$, together can form dione (—C(O)C(O)—).

The present invention also provides a compound of the formula (IV):

wherein at least two of $R^{40}$, $R^{41}$, $R^{42}$, $R^{43}$, and $R^{44}$ are $N_2O_2M$, and the remaining R″, i.e., $R^{40}$, $R^{41}$, $R^{42}$, $R^{43}$, and $R^{44}$ substituent(s) that are not $N_2O_2M$ can be the same or different and are independently selected from the group consisting of hydrogen, an unsubstituted or substituted $C_{1-12}$ straight chain alkyl, an unsubstituted or substituted $C_{3-12}$ branched chain alkyl, an unsubstituted or substituted $C_{3-12}$ straight chain alkenyl, an unsubstituted or substituted $C_{3-12}$ branched chain alkenyl, an unsubstituted or substituted aralkyl, an unsubstituted or substituted aryl, an unsubstituted or substituted acyl, an unsubstituted or substituted alkoxycarbonyl, an unsubstituted or substituted aryloxycarbonyl, carboxamido, an unsubstituted or substituted heteroaryl, sulfonyl, sulfinyl, sulfenyl, phosphoryl, phosphinyl, silyl, cyano, glycosyl, and a cyclic polyamine compound comprising 3 to 6 amino groups that is bound through either a carbon or nitrogen atom in the backbone of the compound;

$R^{45}$-$R^{54}$, i.e., $R^{45}$, $R^{46}$, $R^{47}$, $R^{48}$, $R^{49}$, $R^{50}$, $R^{51}$, $R^{52}$, $R^{53}$, and $R^{54}$, can be the same or different and are independently selected from the group consisting of hydrogen, an unsubstituted or substituted $C_{1-12}$ straight chain alkyl, an unsubstituted or substituted $C_{3-12}$ branched chain alkyl, an unsubstituted or substituted $C_{2-12}$ straight chain alkenyl, an unsubstituted or substituted $C_{3-12}$ branched chain alkenyl, an unsubstituted or substituted alkoxy, an unsubstituted or substituted aralkyl, an unsubstituted or substituted aryl, an unsubstituted or substituted heteroaryl, an unsubstituted or substituted arylamino, an unsubstituted or substituted alkylamino, carboxyalkylamino, carboxydialkylamino, an unsubstituted or substituted acetoxy, an unsubstituted or substituted carboxyalkyl, an unsubstituted or substituted alkylcarbonyl, an unsubstituted or substituted alkylthio, an unsubstituted or substituted alkyloxy, carboxamido, an unsubstituted or substituted alkylcarboxamido, an unsubstituted or substituted dialkylcarboxamido, an unsubstituted or substituted phenoxy, an unsubstituted or substituted benzyloxy, phenylcarbonyl, benzylcarbonyl, silyl, and a cyclic polyamine compound comprising 3 to 6 amino groups that is bound through either a carbon or nitrogen atom in the backbone of the compound;

each M can be the same or different and is a pharmaceutically acceptable cation; and a-e are integers independently from 1 to 3.

Alternatively, two adjacent $R^{40}$, $R^{41}$, $R^{42}$, $R^{43}$, and $R^{44}$ substituent(s) (e.g., $R^{40}$/$R^{41}$, $R^{41}$/$R^{42}$, $R^{42}$/$R^{43}$, $R^{43}$/$R^{44}$, $R^{40}$/$R^{44}$) that are not $N_2O_2M$, together can form dione (—C(O)C(O)—).

A further embodiment of the present invention is a compound of the formula (V):

13

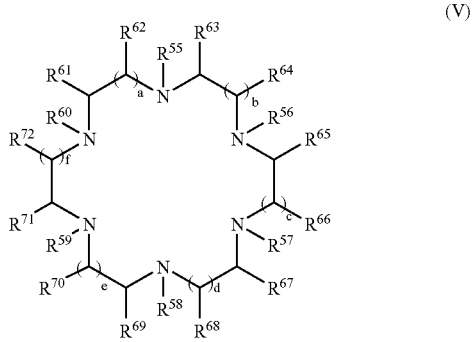

(V)

wherein at least two of $R^{55}$, $R^{56}$, $R^{57}$, $R^{58}$, $R^{59}$, and $R^{60}$ are $N_2O_2M$, and the remaining R″, i.e., $R^{55}$, $R^{56}$, $R^{57}$, $R^{58}$, $R^{59}$, and $R^{60}$, substituent(s) that are not $N_2O_2M$ can be the same or different and are independently selected from the group consisting of hydrogen, an unsubstituted or substituted $C_{1-12}$ straight chain alkyl, an unsubstituted or substituted $C_{3-12}$ branched chain alkyl, an unsubstituted or substituted $C_{3-12}$ straight chain alkenyl, an unsubstituted or substituted $C_{3-12}$ branched chain alkenyl, an unsubstituted or substituted aralkyl, an unsubstituted or substituted aryl, an unsubstituted or substituted acyl, an unsubstituted or substituted alkoxycarbonyl, an unsubstituted or substituted aryloxycarbonyl, carboxamido, an unsubstituted or substituted heteroaryl, sulfonyl, sulfinyl, sulfenyl, phosphoryl, phosphinyl, silyl, cyano, glycosyl, and a cyclic polyamine compound comprising 3 to 6 amino groups that is bound through either a carbon or nitrogen atom in the backbone of the compound;

$R^{61}$-$R^{72}$, i.e., $R^{61}$, $R^{62}$, $R^{63}$, $R^{64}$, $R^{65}$, $R^{66}$, $R^{67}$, $R^{68}$, $R^{69}$, $R^{70}$, $R^{71}$, and $R^{72}$, can be the same or different and are independently selected from the group consisting of hydrogen, an unsubstituted or substituted $C_{1-12}$ straight chain alkyl, an unsubstituted or substituted $C_{3-12}$ branched chain alkyl, an unsubstituted or substituted $C_{2-12}$ straight chain alkenyl, an unsubstituted or substituted $C_{3-12}$ branched chain alkenyl, an unsubstituted or substituted alkoxy, an unsubstituted or substituted aralkyl, an unsubstituted or substituted aryl, an unsubstituted or substituted heteroaryl, an unsubstituted or substituted arylamino, an unsubstituted or substituted alkylamino, carboxyalkylamino, carboxydialkylamino, an unsubstituted or substituted acetoxy, an unsubstituted or substituted carboxyalkyl, an unsubstituted or substituted alkylcarbonyl, an unsubstituted or substituted alkylthio, an unsubstituted or substituted alkyloxy, carboxamido, an unsubstituted or substituted alkylcarboxamido, an unsubstituted or substituted dialkylcarboxamido, an unsubstituted or substituted phenoxy, an unsubstituted or substituted benzyloxy, phenylcarbonyl, benzylcarbonyl, silyl, and a cyclic polyamine compound comprising 3 to 6 amino groups that is bound through either a carbon or nitrogen atom in the backbone of the compound;

each M can be the same or different and is a pharmaceutically acceptable cation; and a-f are integers independently from 1 to 3.

Alternatively, two adjacent $R^{55}$, $R^{56}$, $R^{57}$, $R^{58}$, $R^{59}$, and $R^{60}$ substituent(s) (e.g., $R^{55}/R^{56}$, $R^{56}/R^{57}$, $R^{57}/R^{58}$, $R^{58}/R^{59}$, $R^{59}/R^{60}$, $R^{60}/R^{55}$) that are not $N_2O_2M$, together can form dione (—C(O)C(O)—).

14

During the preparation of the compounds of the invention, intermediates are thought to be formed comprising at least one $N_2O_2$ functional group. For example, during preparation of a diazeniumdiolated compound capable of a biphasic or triphasic release of NO, an intermediate is thought to be formed having only a single $N_2O_2$ functional group. In addition, it is believed that a compound of the invention containing multiple diazeniumdiolate groups at some point forms a mono-diazeniumdiolate compound after administration and the compound begins a phase of NO release. These mono-diazeniumdiolated intermediates of the compounds of the invention, which are believed to be the slow-release NO donors, were previously unknown and comprise part of the invention described herein. A monodiazeniumdiolate can also be formed by adjusting the polarity of the solvent used in the reaction with NO to make it less polar so that the mono-diazeniumdiolate precipitates before a second diazeniumdiolate group can attach itself to the compound. Accordingly, the present invention also provides a compound of the formula (Ia):

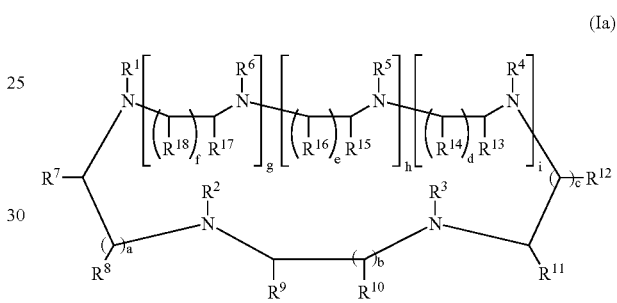

(Ia)

in which one of $R^1$, $R^2$, $R^3$, $R^4$, $R^5$, and $R^6$ are $N_2O_2M$, and the remaining R″, i.e., $R^1$, $R^2$, $R^3$, $R^4$, $R^5$, and $R^6$, substituent(s) that are not $N_2O_2M$ can be the same or different and are independently selected from the group consisting of hydrogen, an unsubstituted or substituted $C_{1-12}$ straight chain alkyl, an unsubstituted or substituted $C_{3-12}$ branched chain alkyl, an unsubstituted or substituted $C_{3-12}$ straight chain alkenyl, an unsubstituted or substituted $C_{3-12}$ branched chain alkenyl, an unsubstituted or substituted aralkyl, an unsubstituted or substituted aryl, an unsubstituted or substituted acyl, an unsubstituted or substituted alkoxycarbonyl, an unsubstituted or substituted aryloxycarbonyl, carboxamido, an unsubstituted or substituted heteroaryl, sulfonyl, sulfinyl, sulfenyl, phosphoryl, phosphinyl, silyl, cyano, glycosyl, and a cyclic polyamine compound comprising 3 to 6 amino groups that is bound through either a carbon or nitrogen atom in the backbone of the compound;

$R^7$-$R^{18}$, i.e., $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$, can the same or different and are independently selected from the group consisting of hydrogen, an unsubstituted or substituted $C_{1-12}$ straight chain alkyl, an unsubstituted or substituted $C_{3-12}$ branched chain alkyl, an unsubstituted or substituted $C_{2-12}$ straight chain alkenyl, an unsubstituted or substituted $C_{3-12}$ branched chain alkenyl, an unsubstituted or substituted alkoxy, an unsubstituted or substituted aralkyl, an unsubstituted or substituted aryl, an unsubstituted or substituted heteroaryl, an unsubstituted or substituted arylamino, an unsubstituted or substituted alkylamino, carboxyalkylamino, carboxydialkylamino, an unsubstituted or substituted acetoxy, an unsubstituted or substituted carboxyalkyl, an unsubstituted or substituted alkylcarbonyl, an unsubstituted or substituted alkylthio, an unsubstituted or substituted alkyloxy, carboxamido, an unsubstituted or substituted alkylcarboxamido, an unsubstituted or substituted dialkylcarboxamido, an unsubstituted or substituted phenoxy, an unsubstituted or substituted benzyloxy, phenylcarbonyl, benzylcarbonyl, silyl, and a cyclic polyamine compound comprising 3 to 6 amino groups that is bound through either a carbon or nitrogen atom in the backbone of the compound;

M is a pharmaceutically acceptable cation;

a-f are integers independently from 1 to 3; and g, h, and i are independently 0 or 1.

Alternatively, two adjacent nitrogen $R^1$, $R^2$, $R^3$, $R^4$, $R^5$, and $R^6$ substituent(s) that are not $N_2O_2M$, together can form dione (—C(O)C(O)—).

The substituent "a cyclic polyamine compound comprising 3 to 6 amino groups" can be represented by the following structure (Ib):

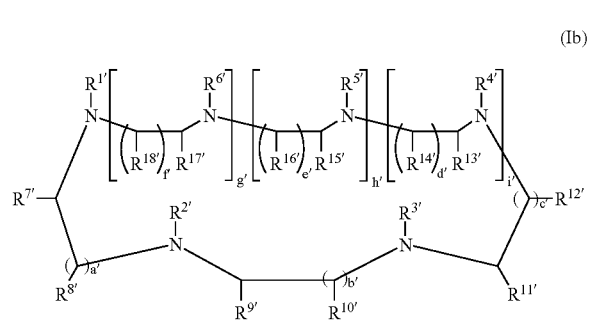

(Ib)

in which $R^{1'}$, $R^{2'}$, $R^{3'}$, $R^{4'}$, $R^{5'}$, and $R^{6'}$ can be the same or different and are independently selected from the group consisting of $N_2O_2M$, hydrogen, an unsubstituted or substituted $C_{1-12}$ straight chain alkyl, an unsubstituted or substituted $C_{3-12}$ branched chain alkyl, an unsubstituted or substituted $C_{3-12}$ straight chain alkenyl, an unsubstituted or substituted $C_{3-12}$ branched chain alkenyl, an unsubstituted or substituted aralkyl, an unsubstituted or substituted aryl, an unsubstituted or substituted acyl, an unsubstituted or substituted alkoxycarbonyl, an unsubstituted or substituted aryloxycarbonyl, carboxamido, an unsubstituted or substituted heteroaryl, sulfonyl, sulfinyl, sulfenyl, phosphoryl, phosphinyl, silyl, cyano, and glycosyl;

$R^{7'}$-$R^{18'}$ can be the same or different and are independently selected from the group consisting of hydrogen, an unsubstituted or substituted $C_{1-12}$ straight chain alkyl, an unsubstituted or substituted $C_{3-12}$ branched chain alkyl, an unsubstituted or substituted $C_{2-12}$ straight chain alkenyl, an unsubstituted or substituted $C_{3-12}$ branched chain alkenyl, an unsubstituted or substituted alkoxy, an unsubstituted or substituted aralkyl, an unsubstituted or substituted aryl, an unsubstituted or substituted heteroaryl, an unsubstituted or substituted arylamino, an unsubstituted or substituted alkylamino, carboxyalkylamino, carboxydialkylamino, an unsubstituted or substituted acetoxy, an unsubstituted or substituted carboxyalkyl, an unsubstituted or substituted alkylcarbonyl, an unsubstituted or substituted alkylthio, an unsubstituted or substituted alkyloxy, carboxamido, an unsubstituted or substituted alkylcarboxamido, an unsubstituted or substituted dialkylcarboxamido, an unsubstituted or substituted phenoxy, an unsubstituted or substituted benzyloxy, phenylcarbonyl, benzylcarbonyl, and silyl;

each M can be the same or different and is a pharmaceutically acceptable cation;

a'-f' are integers independently from 1 to 3; and g', h', and i' are independently 0 or 1.

Alternatively, two adjacent nitrogen $R^{1'}$, $R^{2'}$, $R^{3'}$, $R^{4'}$, $R^{5'}$, and $R^{6'}$ substituent(s) that are not $N_2O_2M$, together can form dione (—C(O)C(O)—).

Covalently joining two or more molecules of any compound of formula (I)-(V), including (Ia), through one or more linkages allows for bis-cyclic polyamino diazeniumdiolate compounds. For example, a preferred compound illustrating a bis-cyclic polyamino diazeniumdiolate compound of the invention has the following structure:

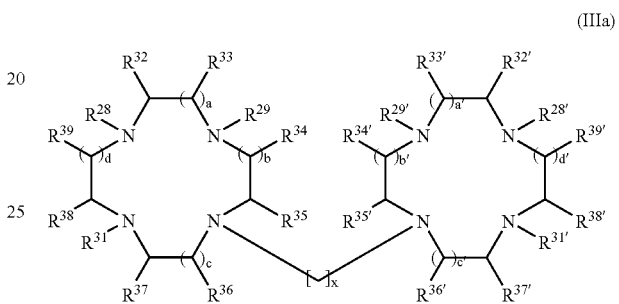

(IIIa)

in which at least one of $R^{28}$, $R^{29}$, and $R^{31}$ and optionally at least one of $R^{28'}$, $R^{29'}$, and $R^{31'}$ are $N_2O_2M$, and x is an integer from 1 to 6.

The intermediate or metabolite of the preferred compound of formula (IIIa) (or those based on formula (Ia)) can include a compound in which at least one of $R^{28}$, $R^{29}$ or $R^{31}$ is $N_2O_2M$ and none, one, two, or each of $R^{28'}$, $R^{29'}$, or $R^{31'}$ are $N_2O_2M$.

For any of the compounds of formulae (I)-(V), including (Ia) and (IIIa), each amino-substituent that is not $N_2O_2M$ or each carbon-substituent can be optionally substituted with 1 to 20 (e.g., 1 to 15, 1 to 10, 1 to 8, 1 to 6, 1 to 5, 1 to 3, etc.) substituents independently selected from the group consisting of alkyl, arylalkyl, alkoxy, aryloxy, arylalkyloxy, acyl, acyloxy, carboxyl, alkoxycarbonyl, aryloxycarbonyl, aralkyloxycarbonyl, carboxamido, arylamino, diarylamino, aralkylamino, amino, alkylamino, dialkylamino, formyl, alkylthio, arylthio, arylalkylthio, aryl and heteroaryl, such as pyrrolyl, furanyl, thiazolyl, pyrazolyl, acridinyl, anthracenyl, benzyl, benzofuranyl, benzothiophenyl, benzoxazolyl, benzopyrazolyl, benzothiazolyl, carbazolyl, chlorophyllyl, cinnolinyl, furanyl, imidazolyl, indolyl, isobenzofuranyl, isoindolyl, isoxazolyl, isothiazolyl, isoquinolinyl, naphthalenyl, oxazolyl, phenanthrenyl, phenanthridinyl, phenothiazinyl, phenoxazinyl, phthalimidyl, phthalazinyl, phthalocyaninyl, porphinyl, pteridinyl, purinyl, pyrazinyl, pyrazolyl, pyridazinyl, pyridinyl, pyrimidinyl, pyrrocolinyl, pyrrolyl, quinolizinium ion, quinolinyl, quinoxalinyl, quinazolinyl, sydnonyl, tetrazolyl, thiazolyl, thiophenyl, thyroxinyl, triazinyl, triazolyl, pyridinyl, or pyrimidinyl, silyl, trialkylsilyl, silyloxy, sulfonyl, sulfinyl, sulfenyl, sulfonato, phosphato, phosphinoxy, trialkylammonium, heterocyclics such as tetrahydrofuranyl, tetrahydropyranyl, piperidinyl, pyrrolidinyl and morpholinol, halo, cyano, nitro, hydroxy, mercapto, cycloalkyl, glycosyl and diazeniumdiolato.

Referring now to terminology used generically herein, the term "alkyl" means a straight-chain or branched alkyl substituent containing from, for example, about 1 to about 12 carbon atoms, preferably from about 1 to about 8 carbon atoms, more preferably from about 1 to about 6 carbon atoms. Examples of such substituents include methyl, ethyl, propyl, isopropyl, n-butyl, sec-butyl, isobutyl, tert-butyl, pentyl, isoamyl, hexyl, octyl, dodecanyl, and the like.

The term "cycloalkyl," as used herein, means a cyclic alkyl substituent containing from, for example, about 3 to about 30 carbon atoms, preferably from about 5 to about 14 carbon atoms, more preferably from about 5 to about 10 carbon atoms, and most preferably from about 5 to about 7 carbon atoms. Examples of such substituents include cyclopropyl, cyclobutyl, cyclopentyl, cyclohexyl, and the like.

The term "halo" or "halogen," as used herein, means a substituent selected from Group VIIA, such as, for example, fluorine, bromine, chlorine, and iodine. Preferably, the halo is bromine or iodine.

The term "aryl" refers to an unsubstituted or substituted aromatic carbocyclic substituent, as commonly understood in the art, and includes monocyclic and polycyclic aromatics such as, for example, phenyl, biphenyl, toluenyl, anisolyl, naphthyl, anthracenyl and the like. An aryl substituent generally contains from, for example, about 3 to about 30 carbon atoms, preferably from about 6 to about 18 carbon atoms, more preferably from about 6 to about 14 carbon atoms and most preferably from about 6 to about 10 carbon atoms. It is understood that the term aryl applies to cyclic substituents that are planar and comprise $4n+2$ $\pi$ electrons, according to Hückel's Rule.

The term "heteroaryl" means a substituent defined by an aromatic heterocyclic ring, as is commonly understood in the art, including monocyclic and polycyclic heteroaryls containing from, for example, about 3 to about 30 carbon atoms, preferably from about 5 to about 10 carbon atoms, more preferably from about 5 to about 6 carbon atoms. Monocyclic heteroaryls include, for example, imidazolyl, thiazolyl, pyrazolyl, pyrrolyl, furanyl, pyrazolinyl, thiophenyl, oxazolyl, isoxazolyl, pyridinyl, pyridonyl, pyrimidinyl, pyrazinyl, and triazinyl substituents. Polycyclic heteroaryls include, for example, quinolinyl, isoquinolinyl, indolyl, purinyl, benzimidazolyl, benzopyrrolyl, and benzothiazolyl.

The term "alkoxy" embraces linear or branched alkyl groups that are attached to divalent oxygen. The alkyl group is the same as described herein. Examples of such substituents include methoxy, ethoxy, t-butoxy, and the like. The aryl group is the same as described herein. The term "aryloxy" refers to substituents that have an aryl group attached to divalent oxygen. Examples of such substituents include phenoxy.

The term "alkylthio" as used herein, denotes a substituent with an alkyl group directly attached to a divalent sulfur atom. The alkyl group is the same as described herein. Examples of such substituents include methylthio, ethylthio, and the like. Similarly, the term "arylthio" as used herein, denotes a substituent with an aryl group directly attached to a divalent sulfur atom. The aryl group is the same as described herein.

The term "carboxyl" refers to the group —C(O)OH. The term "carboxyalkyl" refers to the group —RC(O)OH that is connected to the compound through the alkyl R group. The term "carboxyalkyloxy" refers to the group —ORC(O)OH, in which the R is an alkyl (e.g., $(CH_2)_n$ alkylene group, n is 1 to 12) group.

The term "alkylamino" refers to a secondary amine substituent with one hydrogen and one alkyl group directly attached to a trivalent nitrogen atom. In addition, the term "alkylamino" also refers to a tertiary amine substituent with two of the same or different alkyl groups directly attached to a trivalent nitrogen atom. The alkyl group is the same as described herein.

For any of the compounds of formulae (I)-(V), including (Ia) and (IIIa), the counterion, M, is any noncovalently bound counterion capable of balancing the charge. Preferably, for biological applications, the counterion is a pharmaceutically acceptable counterion. The only requirement for the pharmaceutically acceptable counterion chosen is biological compatibility in an animal, such as a human. Biologically acceptable counterions include alkali metals such as sodium ion, potassium ion, lithium ion, and the like; alkaline earth metals such as magnesium ion, calcium ion, and the like; Group III metals such as aluminum ion; Group IV metals such as tin ion; and transition metals, including iron ion, copper ion, manganese ion, zinc ion, cobalt ion, vanadium ion, molybdenum ion, platinum ion, and the like. Non-metal counterions include quaternary ammonium ions. Metal ions that may be considered toxic may, nevertheless, be pharmaceutically acceptable and thus within the scope of the invention if their complexes with the diazeniumdiolates are sufficiently potent pharmacologically and the total concentration of the metal counterion upon dosing is below the toxic threshold of the metal.

In another embodiment, M can be an organic group that is covalently bound to the terminal oxygen of the diazeniumdiolate group. For illustrative purposes only, a compound of formula (II), in which $R^{21}$-$R^{27}$ are H; a, b, and c are each 1; $R^{19}$ is $N_2O_2Na$; and $R^{20}$ is $N_2O_2Me$ could be prepared by an adaptation of the method used for the mixed piperazine bis-diazeniumdiolate of Example III in U.S. Pat. No. 5,721,365, by: (1) exposing this bis-tBoc derivative of 1,4,7-triazacyclononane to NO; (2) methylating the product; (3) removing the tBoc groups; and (4) exposing the product to NO. A wide variety of analogous new compounds can be synthesized, in which at least one M is an organic group (e.g., alkyl, vinyl, etc.), provided that M is not an aryl, a heteroaryl or a sugar.

M can also be a metal center that is covalently bound to at least one oxygen of at least one diazeniumdiolate group and can also be covalently bound to one or more of the ring nitrogens.

A preferred compound of formula (I) is one in which $R^7$-$R^{18}$ are each hydrogen.

A preferred compound of formula (III) is

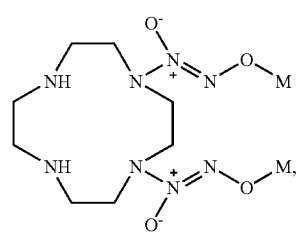

where each M is the same or different and is a cation. Preferably, for physiological applications, M is sodium or ammonium.

Another preferred compound of formula (III) is

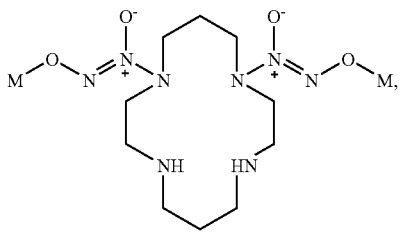

where each M is the same or different and is a cation. Preferably, for physiological applications, M is sodium or ammonium.

The invention provides a cyclic polyamine compound comprising at least three amino groups, wherein at least two of the amino groups are covalently bound to a nitrogen oxide-releasing group of the formula $N_2O_2M$, in which M is a pharmaceutically acceptable cation. The invention also provides a compound that has a polyphasic release of nitric oxide, wherein any subsequent release of nitric oxide has a rate that is at least about 3 times smaller than an initial rate of nitric oxide release. The rate of NO release can be determined by any suitable method. For example, the rate of NO release can be measured by the decrease in 250-252 mm absorbance over time at 37° C. as previously described by Keefer et al., "NONOates" (1-Substituted Diazen-1-ium-1,2-diolates) as Nitric Oxide Donors: Convenient Nitric Oxide Dosage Forms. *Methods in Enzymology,* 1996, 268, 281-293.

Another aspect of the invention is a pharmaceutical composition comprising a pharmaceutically acceptable carrier and a compound that releases at least about two moles of nitric oxide within about 2 minutes under physiological conditions and at least about two additional moles of nitric oxide beyond about 5 minutes under physiological conditions. Preferably, for compounds that have a polyphasic release of NO, the initial phase release of nitric oxide occurs within less than about 2 minutes (e.g., instantaneous release, 30 seconds, one minute, one minute and 30 seconds, etc.), and the additional release(s) of nitric oxide occurs beyond at least about 5 minutes, as measured from time zero of the initial phase release, under suitable conditions, e.g., physiological conditions. More preferably, the initial phase release of nitric oxide occurs within less than 20 minutes and the additional release(s) of nitric oxide occurs beyond at least 1 hour under suitable conditions, e.g., physiological conditions. Preferably, for compounds that have a polyphasic release of NO, any subsequent release of NO has a rate that is at least about 3 times (e.g., at least about 5 times, at least about 10 times, at least about 20 times, at least about 50 times, at least about 100 times, at least about 1000 times, etc.) smaller than the initial rate of NO release. The NO release profiles are preferably measured under physiological conditions (e.g., pH 7.4 and 37° C. for a human) as the rates are measured as a function of the half-life of NO. Such measurements can occur at other temperatures, for example, room temperature, which may affect the rate of NO release. Preferably compounds that have a biphasic release of NO, as described herein, do not include piperazine bisdiazeniumdiolate. Preferably, compounds that have a polyphasic release of NO, as described herein, have an initial release of NO on a time scale such that immediate treatment of a disorder is rendered and any subsequent release of NO by the compound can treat or prevent any lingering or reappearance of symptoms of such disorders.

The term "polyphasic release of nitric oxide" includes the term "biphasic release of nitric oxide" and means that the compound has an initial phase release of NO on a short time scale and at least one additional phase release of NO under suitable conditions, e.g., physiological conditions, over a longer time scale. If the compound has two diazeniumdiolate functional groups ($N_2O_2^-$) on the same cyclic polyamine compound, then a biphasic release of NO can be expected from the compounds of the invention. Similarly, three diazeniumdiolate groups in a compound of the invention would be expected to provide a triphasic release of NO and so on. However, it should be recognized that when compounds have multiple (i.e., two or more) diazeniumdiolate groups, it may not be possible to separate the kinetics and accurately measure the half-life of the second, third, etc. releases of NO. It is possible that the second, third, etc. releases of NO would have release rates that cannot be independently measured because of overlap, etc. The important factor is that the initial phase release of NO is on a time scale that is distinct from the additional phase release(s) of NO. A short time scale is generally calculated on a seconds or minutes scale. For example, in biological applications, a short time scale of NO release is preferably less than 60 min, more preferably less than 45 min, even more preferably less than 30 min, and most preferably less than 20 min, upon administration to an animal (e.g., a mammal such as a human). A long time scale is generally calculated on an hours or days scale. For example, in biological applications, a long time scale of NO release is preferably more than 1 h, more preferably more than 1.5 h, even more preferably more than 2 h, and most preferably more than 2.5 h, after administration to an animal (e.g., a mammal such as a human). A short time scale of NO release can be measured in terms of seconds (e.g., less than 60 sec, less than 45 sec, less than 30 sec, less than 20 sec, less than 10 sec), compared to a long time scale measured in minutes (e.g., more than 1 min, more than 2 min, more than 5 min, more than 10 min, more than 15 min, more than 20 min, etc.).

In order to prepare the compounds of the invention, the cyclic polyamine is first obtained. Many cyclic polyamines can be obtained commercially and some compounds are known in the literature (see, for example, Meunier, et al., *Can. J. Chem.,* 1995, 73, 685-695; Militsopoulou, et al., *Tetrahedron Lett.,* 2002, 43, 2593-2596; U.S. Pat. No. 5,587,451; Panetta et al., *Tetrahedron Lett.,* 1992, 33(38), 5505-5508; Atkins et al., *Organic Synthesis, Collective Volume VI,* 1988, 652-661; Barefield et al., *Inorg. Chem.,* 1976, 15(6) 1370-1377; Reed et al., *Organic Synthesis,* 2000, 78, 73-81; Handel et al., *J. Chem. Soc., Perkin Trans.* 1, 1999, 3499-3505; Yang et al., *Tetrahedron Lett.,* 2003, 44, 2481-2483; Sherry et al., *Synthesis* 1997, 759-763; and Sisti et al., *Tetrahedron Lett.,* 2000, 41, 6527-6530). Once a suitable cyclic polyamine has been prepared or commercially purchased, it may then be reacted with nitric oxide to give a compound of the invention. The nitric oxide-releasing cyclic polyamine compounds of the present invention are obtainable by reacting suitable cyclic polyamines with nitric oxide in a method similar to that taught by Drago et al. (*J. Am. Chem. Soc.,* 1961, 83: 1819-1822). Drago et al.'s method, if used to prepare the inventive compounds herein disclosed, would entail bubbling nitric oxide into a cold solution (about −78° C.) of the appropriate cyclic polyamine and allowing the formed product to precipitate. Alternatively, high pressure techniques also are taught by Drago et al. in the cited reference for forming nitric acid adducts, and the same are generally applicable herein. The cited Drago et al. reference is incorporated by reference herein. This technique is illustrated in Examples 1 and 2 below.

In addition to the methods described above, the present invention provides a novel method of preparing site-specific diazeniumdiolation of polyaza macrocycles of the formulae (I)-(V), including (Ia) and (IIIa). According to this method, various protecting groups are employed to provide selective diazeniumdiolation of specific nitrogen sites within the macrocycle. Any suitable protecting group can be used, but typically the protecting group will be specific for nitrogen. Typical nitrogen protecting groups include benzyloxycarbonyl ("Cbz"), t-butoxycarbonyl ("t-BOC"), 9-fluorenylmethoxycarbonyl ("Fmoc"), phthalimides ("Pht"), N-sulfonyl derivatives, oxamide derivatives, and carbonyl derivatives (e.g., formyl, trifluoroacetate, methoxycarbonyl, ethoxycarbonyl, t-butoxycarbonyl). See Greene et al., "Protective Groups in Organic Synthesis, $3^{rd}$ Ed.," Wiley-Interscience (May 15, 1999) and P. J. Kocienski, "Protecting Groups (Thieme Foundations of Organic Chemistry Series)," Thieme Medical Publishers (Sep. 1, 2000), which are incorporated by reference herein, for additional examples and methods of using suitable protecting groups. The protecting groups may or may not be removed after the macrocycle is diazeniumdiolated.

Accordingly, the present invention provides a method of preparing a diazeniumdiolated compound of any of formula (I)-(V), including (Ia) and (IIIa), comprising: (a) providing a cyclic polyamine, (b) selectively protecting one or more aza groups with at least one protecting group, (c) exposing the protected cyclic polyamine to nitrogen oxide gas in the presence of a base, and (d) obtaining the diazeniumdiolated compound. More specifically, a cyclic polyamine can be obtained commercially or by synthesis methods described herein. Using known literature techniques or techniques described herein, at least one aza group on the cyclic polyamine is protected with at least one protecting group. A solution or slurry, as appropriate, of the protected cyclic polyamine is prepared in a solution of strong base in a solvent contained in a Parr pressure bottle. Nitrogen, argon, or other inert gas is passed through the apparatus and bubbled through the solution for a time sufficient to create an inert environment. The bottle is placed into the reactor system (see, for example, Hrabie et al., *J. Org. Chem.*, 58: 1472 (1993)), further flushed with inert gas, vented, and nitric oxide gas is admitted to a pressure suitable for reacting with the starting material. The reaction is stirred for a time sufficient to allow the reaction to go to completion at room temperature with the addition of NO as needed to maintain the reservoir pressure. Excess NO is then vented, and inert gas is bubbled through the resultant slurry for several minutes. The product is isolated by filtration, washed with solvent (e.g., methanol and/or ethyl ether), and dried in vacuo, for example, for several hours or overnight, as appropriate. The products typically are stored in glass jars in a refrigerator.

Without wishing to be bound by any particular theory, it is believed that the selectivity of the protecting group(s) arises from the synthetic conditions employed. For instance, a pH of about 2-3 can selectively provide a 1,7 di-protected species. In theory, the acidic medium protonates two of the nitrogens. Usually the 4- and 11-positions are preferentially protonated because of electrostatic repulsion of the two positive charges. This leaves the opposite two nitrogens (at the 1- and 7-positions) open for protection. In another illustrative example, for a 1,4,7 tri-protected species, it is hypothesized that one basic nitrogen is necessary for the formylation/acetylation of the other three nitrogens, and therefore the basic nitrogen intramolecularly assists in the protection process.

The base used for the reaction initiates the reaction without itself reacting directly with NO. Preferably, the base is a metal alkoxide of the formula MOR, wherein M is a cation, such as alkali metals (e.g., sodium ion, potassium ion, lithium ion), alkaline earth metals (e.g., magnesium ion, calcium ion), Group III metals (e.g., aluminum ion), Group IV metals (e.g., tin ion), and transition metals (e.g., iron ion, copper ion, manganese ion, zinc ion, cobalt ion, vanadium ion, molybdenum ion, platinum ion). Non-metal cations include quaternary ammonium ions. Generally, R is an unsubstituted or substituted $C_{1-12}$ straight chain alkyl, an unsubstituted or substituted $C_{3-12}$ branched chain alkyl, a phenyl, naphthyl, or $C_{1-12}$ trialkylsilyl. Preferably R is methyl. Illustrative bases suitable for use in the practice of the method include sodium methoxide, potassium isopropoxide, sodium t-butoxide, potassium t-butoxide, lithium trimethylsilanoate, sodium trimethylsilanoate, and potassium trimethylsilanoate.

Once the desired nitric oxide adduct according to the present invention has been prepared, a pharmaceutically acceptable salt thereof, as defined herein, can be prepared if desired. Exemplary of techniques used to prepare such salts would be the preparation of the potassium salt of one of the formulae (I)-(V), including (Ia) and (IIIa) by reacting the same with, for example, potassium hydroxide in an ethanol or similar solution. Similarly, the sodium, calcium and magnesium salts, among others, could be prepared.

Another aspect of the invention provides compositions, including pharmaceutical compositions, comprising a diazeniumdiolate of any of formulae (I)-(V), including formulae (Ia) and (IIIa). Preferably, the pharmaceutical compositions further comprise a pharmaceutically acceptable carrier. The pharmaceutically acceptable carriers described herein, for example, vehicles, adjuvants, excipients, and diluents, are well-known to those skilled in the art and are readily available to the public.

One skilled in the art will appreciate that suitable methods of administering a diazeniumdiolate composition of the present invention to an animal, e.g., a mammal such as a human, are known, and, although more than one route can be used to administer a particular composition, a particular route can provide a more immediate and more effective reaction than another route. Pharmaceutically acceptable carriers are also well known to those who are skilled in the art. The choice of carrier will be determined, in part, both by the particular composition and by the particular method used to administer the composition. Accordingly, there are a wide variety of suitable formulations of the pharmaceutical compositions of the present invention.

Formulations suitable for oral administration can consist of (a) liquid solutions, such as an effective amount of the diazeniumdiolate dissolved in diluents, such as water or saline, (b) capsules, sachets or tablets, each containing a predetermined amount of the active ingredient, as solids or granules, (c) suspensions in an appropriate liquid, and (d) suitable emulsions.

Tablet forms can include one or more of lactose, mannitol, cornstarch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such carriers as are known in the art.

The diazeniumdiolates of the present invention, alone or in combination with other suitable components, can be made into aerosol formulations to be administered via inhalation.

These aerosol formulations can be placed into pressurized acceptable propellants, such as dichlorodifluoromethane, propane, nitrogen, and the like.

Formulations suitable for parenteral administration include aqueous and non-aqueous solutions, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The dose administered to an animal, particularly a human, in the context of the present invention should be sufficient to effect a therapeutic response in the animal over a reasonable time frame. The dose will be determined by the strength of the particular compositions employed (taking into consideration, at least, the rate of NO evolution, the extent of NO evolution, and the bioactivity of any decomposition products derived from the diazeniumdiolates) and the condition of the animal (e.g., human), as well as the body weight of the animal (e.g., human) to be treated. The size of the dose also will be determined by the existence, nature, and extent of any adverse side effects that might accompany the administration of a particular composition. A suitable dosage for internal administration is 0.01 to 100 mg/kg of body weight per day, such as 0.01 to 35 mg/kg of body weight per day or 0.05 to 5 mg/kg of body weight per day. A suitable concentration of the compound in pharmaceutical compositions for topical administration is 0.05 to 15% (by weight), preferably 0.02 to 5%, and more preferably 0.1 to 3%.

The invention also provides methods of using a nitric oxide-releasing diazeniumdiolate of formulae (I)-(V), including formulae (Ia) and (IIIa). In one embodiment of the invention is provided a method of treating an animal, e.g., a mammal such as a human, having a biological disorder in which a polyphasic release of nitric oxide is beneficial. The method comprises administering to the animal (e.g., human) in need thereof an amount of a compound of any of formulae (I)-(V), including formulae (Ia) and (IIIa), or a substrate or composition thereof sufficient to treat the biological disorder in the animal (e.g., human). In this embodiment, "biological disorder" can be any biological disorder, including ischemic heart disease, sexual dysfunction, metal toxicity, hypertension, cerebral vasospasm, restenosis, cancer, excessive platelet aggregation and adhesion, and a biological disorder due to a genetic defect or infection with an infectious agent, such as a virus, bacterium, fungus or parasite, as long as the disorder is treatable with nitric oxide, preferably treatable with a polyphasic release of nitric oxide. The treatment can be prophylactic or therapeutic. By "prophylactic" or "prevent" is meant any degree of inhibition of the onset of the effects of the disorder, including complete inhibition. By "therapeutic" or "treatment" is meant any degree of beneficial effects on the disorder in the mammal (e.g., human).

Without wishing to be bound by any particular theory and with one illustrative example of using the compound of the invention in the inhibition of restenosis, it is believed that a poly- or biphasic NO-releaser would have the advantage of (1) first generating NO at a high rate at the acute phase of angioplasty injury (i.e., at the moment the vessel wall is torn open by inflating the balloon and/or expanding the stent) to keep the platelets from adhering to the wound as it is freshly exposed to the blood and to prevent the platelets from activating to inject mitogens and growth factors into the wound that could begin the program of restenotic vessel wall thickening (Baek et al., Circulation, in press). Such compounds would then (2) provide a slower, more prolonged flux of NO to inhibit the proliferation of vascular smooth muscle cells that is the primary contributor to restenosis in many cases occurring 6-12 months following inflation of the balloon (Mooradian et al, *J. Cardiovasc. Pharmocol.,* 1995, 25: 674-678).

Similar benefits might be expected to result from polyphasic NO release for a host of other disorders, especially those that can be treated by modulating cyclic GMP levels. Acute respiratory crises might be treated with an effective amount of a poly- or biphasic NO donor whose first phase very rapidly dilates the airways and quickly reverses the associated pulmonary hypertension and whose subsequent phase(s) provide(s) the "maintenance dose" required to sustain these beneficial effects. A similar outcome is anticipated for testing impotence; Champion et al. (*J. Urol.,* 1999, 161: 2013-2019) have shown that a single dose of a very short half-life (e.g., about 2 sec) NO donor induces erections in male cats lasting more than 15 min, and that the maintenance phase NO release of a polyphasic NO donor would significantly strengthen and extend the effect. Similar benefits would be expected in modulating cervical ripening (Facchinetti et al., *Hum. Reprod.,* 2001, 15: 2224-2227), ischemia/reperfusion injury, female sexual arousal, antimicrobial effects, clotting disorders, and angiogenesis.

The compounds and compositions of the invention are useful for treating an animal, e.g., a mammal such as a human, for infection with, for example, a virus (e.g., hepatitis, HIV), a bacterium, or a parasite. The method comprises administering to the animal, e.g., human, an amount of a compound of any of formulae (I)-(V), including (Ia) and (IIIa), of the invention or composition thereof sufficient to treat the infection in the animal.

A preferred method of treating an infection, in particular HIV and hepatitis (e.g., hepatitis B), includes administering a mutual prodrug of any of the compounds of formulae (I)-(V), including (Ia) and (IIIa). An especially preferred method includes administering a diazeniumdiolate of formula (III) or (IIIa), sometimes referred to as cyclams. Because cyclams are known to have therapeutic effects (see, for example, *J. Med. Chem.,* 2002, 45: 469-477; *Biol. Pharm. Bull.,* 1994, 17(2): 243-50; Watanabe et al., *Jpn. J. Pharmacol.,* 1982, 32(2): 394-6; and Hantz et al., *Antimicrobial Agents and Chemotherapy,* 1997, 41(11): 2579-2581), such as alleviating nickel-induced biochemical and trace metal alteration in the liver and kidney of nickel-treated rats, both components of a compound of formula (III) or (IIIa) (i.e., the $N_2O_2^-$ moieties and the cyclam base structure) would be useful for the treatment of certain biological disorders, and thus such compounds can be characterized as mutual prodrugs. In addition, bicyclams have been shown to be potent and selective inhibitors of HIV (see, for example, De Clercq et al., *Proc. Natl. Acad. Sci. USA,* 1992, 89: 5286-5290; *Antimicrob. Agents Chemother.,* 1994, 38(4): 668-74; *Molecular Pharmacology,* 1999, 55: 67-73.

The compounds of any of formulae (I)-(V), including (Ia) and (IIIa), or compositions thereof are useful for treating a mammal, such as a human, for cancer. The method comprises administering to the mammal, e.g., human, a cancer-treatment effective amount of a compound of any of formulae (I)-(V), including (Ia) and (IIIa), or a substrate or composition thereof, whereupon the mammal is treated for cancer. Cyclic polyamines, such as 1,4,7,10-tetraazacyclododecane and cyclam derivatives, have been shown to inhibit leukemic L1210 tumor cell growth (see, for example, Sibert et al., *Chem. Comm.*, Jan. 10, 2002, 154-155). In addition, thirteen- and fourteen-membered tetraaza-macrocyclic ligands complexed to copper and covalently bound to an antibody have been used to treat breast and colorectal cancer (see, for example, Morphy et al., *J. Chem. Soc., Chem. Commun.,* 1989, 792-794).

The method of treating cancer with a compound of any of formulae (I)-(V), including (Ia) and (IIIa), can be used in combination with other known treatment methods, such as radiation, surgery, or the administration of other active agents, such as adjuvants or other anti-cancer agents and their prodrugs. Examples of cyotoxic agents and their prodrugs include genistein, okadaic acid, 1-β-D-arabinofuranosyl-cytosine, arabinofuranosyl-5-aza-cytosine, cisplatin, carboplatin, actinomycin D, asparaginase, bis-chloro-ethyl-nitroso-urea, bleomycin, chlorambucil, cyclohexyl-chloro-ethyl-nitroso-urea, cytosine arabinoside, daunomycin, etoposide, hydroxyurea, melphalan, mercaptopurine, mitomycin C, nitrogen mustard, procarbazine, teniposide, thioguanine, thiotepa, vincristine, 5-fluorouracil, 5-fluorocytosine, adriamycin, cyclophosphamide, methotrexate, vinblastine, doxorubicin, leucovorin, taxol, anti-estrogen agents such as tamoxifen, intracellular antibodies against oncogenes, the flavonol quercetin, Guan-mu-tong extract, retinoids such as fenretinide, nontoxic retinoid analogues such as N-(4-hydroxyphenyl)-retinamide (HPR), and monoterpenes such as limonene, perillyl alcohol and sobrerol.

The method of treating cancer with a compound of any of formulae (I)-(V), including (Ia) and (IIIa), or substrate or composition thereof can be combined with still other methods of prophylactic and therapeutic treatment. Such methods include those that target destruction of cancer cells, e.g., by targeting of cell-surface markers, receptor ligands, e.g., ligands to gastrin-releasing peptide-like receptors, tumor-associated antigens, e.g., the 57 kD cytokeratin or the antigen recognized by the monoclonal antibody GB24, the extracellular matrix glycoprotein tamascin, antisense constructs to mRNA of oncogenes such as c-fos, homeobox genes that are expressed in cancer cells but not normal cells, tumor-infiltrating lymphocytes that express cytokines, RGD-containing peptides and proteins, which are administered following surgery, lipophilic drug-containing liposomes to which are covalently conjugated monoclonal antibodies for targeting to cancer cells, low fat diet, moderate physical exercise and hormonal modulation. For prostate cancer, anti-testosterone agents can be used as well as inhibitors of cellular proliferation produced by prostatic stromal cells and C-CAM, an epithelial cell adhesion molecule.

The cyclic polyamine diazeniumdiolates of the invention are useful for treating an inanimate object for the presence of a potentially infectious virus, bacterium, or parasite. The method comprises contacting the inanimate object with an amount of an diazeniumdiolate of formula (I), (Ia), (II), (III), (IIIa), (IV), or (V) of the invention or compositions thereof sufficient to reduce the presence of the potentially infectious virus, bacterium or parasite. By "potentially infectious" is meant the capability of infecting an animal, e.g., a mammal such as a human.

In another aspect of the invention, a nitric oxide-releasing cyclic polyamine compound of any of formulae (I)-(V), including (Ia) and (IIIa), can be bound to a polymer, similar to those described in, for example, U.S. Pat. Nos. 5,405,919, 5,525,357, 5,632,981, 5,650,447, 5,676,963, 5,691,423, and 5,718,892, and incorporated herein by reference. Preferably, the diazeniumdiolate is bound to the polymer through a carbon substituent on the diazeniumdiolate compound of the invention. By "bound to a polymer" it is meant that the nitric oxide-releasing cyclic polyamine, such as those described by formulae (I)-(V), including (Ia) and (IIIa), is associated with, part of, incorporated with, or contained within the polymer matrix physically or chemically. Physical association or bonding of the nitric oxide-releasing cyclic polyamine to the polymer may be achieved by co-precipitation of the polymer with the nitric oxide-releasing cyclic polyamine as well as by covalent bonding of the complex to the polymer. Chemical bonding of the nitric oxide-releasing cyclic polyamine to the polymer may be by, for example, covalent bonding of the cyclic polyamine moiety of the nitric oxide-releasing cyclic polyamine to the polymer such that the cyclic polyamine residue to which the NONO group is attached forms part of the polymer itself, i.e., is in the polymer backbone, or is attached to a group or groups pendant to the polymer backbone. If the diazeniumdiolates of the present invention are chemically bound to the polymer/biopolymer, then the diazeniumdiolates are bound to the polymer/biopolymer by at least one functional group on the polymer or biopolymer. Preferably, more than one diazeniumdiolate compound of the present invention is chemically bound per molecule of the polymer/biopolymer. The manner in which the nitric oxide-releasing cyclic polyamine is associated, part of, or incorporated with or contained within, i.e., "bound" to the polymer, is inconsequential to the invention and all means and degrees of association, incorporation or bonding are contemplated herein.

Any of a wide variety of polymers can be used in the context of the invention. Illustrative of polymers suitable for use in the invention are polyolefins, such as polystyrene, polypropylene, polyethylene, polytetrafluorethylene, polyvinyl chloride or polyvinylidene difluoride, and polyethers such as polyethylene glycol, polysaccharides such as dextran, polyesters such as poly(lactide/glycolide), polyamides such as nylon, polyurethanes, polyethylenimine, biopolymers such as peptides, polypeptides, enzymes, polysaccharides, proteins, oligonucleotides, antibodies and nucleic acids, starburst dendrimers, and the like. The term "biopolymers", as used herein, also include monomeric units of larger biopolymers such as monosaccharides, amino acids or nucleotides.

Another aspect of this invention includes a substrate that comprises a nitric oxide-releasing cyclic polyamine compound of the invention, such as, for example, where the compound is part of, bound to, or coated on the substrate. Preferably the substrate has moieties that allow for chemical bonding of the NO-releasing cyclic polyamine to the substrate. See, for example, U.S. Patent Application No. 2001/0003599, which is incorporated herein by reference in its entirety.

The substrate can be of any suitable biocompatible material, such as metal, glass, ceramic, or plastic or rubber. Preferably, the substrate is metal. The substrate used in the preparation of the medical device can be derived from any suitable form of a biocompatible material, such as, for example, a sheet, a fiber, a tube, a fabric, an amorphous solid, an aggregate, dust or the like.

Metal substrates suitable for use in the invention include, for example, stainless steel, nickel, titanium, tantalum, aluminum, copper, gold, silver, platinum, zinc, silicon, magnesium, tin, alloys, coatings containing any of the above and combinations of any of the above. Also included are such metal substrates as galvanized steel, hot dipped galvanized steel, electrogalvanized steel, annealed hot dipped galvanized steel and the like. Preferably, the metal substrate is stainless steel.

Glass substrates suitable for use in the invention include, for example, soda lime glass, strontium glass, borosilicate glass, barium glass, glass-ceramics containing lanthanum as well as combinations thereof.

Ceramic substrates suitable for use in the invention include, for example, boron nitrides, silicon nitrides, aluminas, silicas, combinations thereof, and the like.

Plastic substrates suitable for use in the invention include, for example, acrylics, acrylonitrile-butadiene-styrene, polyphenylene oxides, polyimides, polystyrene, polypropylene, polyethylene, polytetrafluoroethylene, polyethylenimine, polyesters, polyethers, polylactones, polyurethanes, polycarbonates, polyethylene terephthalate, as well as copolymers and combinations thereof. Typical rubber substrates suitable for use in the invention include, for example, silicones, fluorosilicones, nitrile rubbers, silicone rubbers, fluorosilicone rubbers, polyisoprenes, sulfur-cured rubbers, isoprene-acrylonitrile rubbers, and the like. Silicones, fluorosilicones, polyurethanes, polycarbonates, polylactones, and mixtures or copolymers thereof are preferred plastic or rubber substrates because of their proven bio- and hemocompatability when in direct contact with tissue, blood, blood components, or bodily fluids.

Other suitable substrates include those described in WO 00/63462, and incorporated herein by reference.

The invention provides medical devices which are capable of releasing nitric oxide when in use, but which are otherwise inert to nitric oxide release. The nitric oxide-releasing medical devices of the invention may comprise $N_2O_2^-$ functional groups as part of the substrate, bound to the substrate, or coated onto the substrate. Preferably, the $N_2O_2^-$ functional groups are bound or coated onto the substrate through the compounds of formulae (I) through (V), including (Ia) and (IIIa). The term "bound" as used herein includes covalent bonds, ionic bonds, van der Waal forces, hydrogen bonding, electrostatic bonding, and all other methods for attaching organic chemical functional groups to a substrate.

A "medical device" refers to any device having surfaces that contact tissue, blood, or other bodily fluids in the course of their use or operation, which are found in or are subsequently used in patients or animals. Medical devices include, for example, extracorporeal devices for use in surgery, such as blood oxygenators, blood pumps, blood storage bags, blood collection tubes, blood filters including filtration media, tubing used to carry blood and the like which contact blood which is then returned to the patient or animal. Medical devices also include endoprostheses implanted in a human or animal body, such as vascular grafts, stents, pacemaker leads, heart valves, and the like, that are implanted in blood vessels or the heart. Medical devices also include devices for temporary intravascular use such as catheters, guide wires, amniocentesis and biopsy needles, cannulae, drainage tubes, shunts, sensors, transducers, probes and the like which are placed into the blood vessels, the heart, organs or tissues for purposes of monitoring or repair or treatment. Medical devices also include prostheses such as artificial joints such as hips or knees as well as artificial hearts. Preferably, the substrate is a stent, in which the stent comprises a compound of any of formulae (I)-(V), including (Ia) and (IIIa). The compound can form part of the stent itself, can be bound to the stent and/or coated on the stent.

The following examples further illustrate the invention but, of course, should not be construed as in any way limiting its scope.

The nuclear magnetic resonance spectra were recorded with a 400 MHz Varian Unity Plus NMR spectrometer. Due to the instability of the shorter-lived phase of the compounds in solution, the spectra were recorded in $D_2O$ with NaOD. The ultraviolet spectra were recorded on a Hewlett Packard Model 8451A diode array spectrometer and were obtained in a 0.01 M NaOH solution to avoid any degradation. Melting points were taken on a Fisher Johns melting point apparatus and are uncorrected. Unless otherwise noted, the cyclic polyamines were purchased from Aldrich Chemical Co. (Milwaukee, Wis.) or Strem Chemicals Inc (Newburyport, Mass.). The synthesis of various cyclic polyamines can be found in the literature (see, for example, Meunier, et al., *Can. J. Chem.*, 1995, 73, 685-695; Militsopoulou, et al., *Tetrahedron Lett.*, 2002, 43, 2593-2596; U.S. Pat. No. 5,587,451; Panetta et al., *Tetrahedron Lett.*, 1992, 33(38), 5505-5508; Atkins et al., *Organic Synthesis, Collective Volume VI*, 1988, 652-661; Barefield et al., *Inorg. Chem.*, 1976, 15(6) 1370-1377; Reed et al., *Organic Synthesis*, 2000, 78, 73-81; Handel et al., *J. Chem. Soc., Perkin Trans. 1*, 1999, 3499-3505; Yang et al., *Tetrahedron Lett.*, 2003, 44, 2481-2483; Sherry et al., *Synthesi,s* 1997, 759-763; and Sisti et al., *Tetrahedron Lett.*, 2000, 41, 6527-6530). The reaction solvent for the compound of Example 1 was anhydrous grade (Aldrich), but all the other solvents were reaction grade. The nitric oxide gas was purchased from Matheson Gas Products. Elemental analyses were performed by Altantic Microlab Inc. (Norcross, Ga.). Chemiluminescence measurements of nitric oxide were preformed with a Thermal Energy Analyzer Model 502A from Thermedics Inc. (Woburn, Mass.).

The compounds of the invention, including diazeniumdiolates, are physiologically active and should be handled with care. While these compounds show no signs of instability during routine handling under ambient conditions, the compounds may decompose and release toxic NO gas upon exposure to $CO_2$, water, or acid vapor. Preferably, the compounds are stored in closed containers under refrigeration.

EXAMPLE 1

This example illustrates the synthesis of 1,4,8,11-tetraazacyclotetradecane-1,11-bisdiazeniumdiolate.

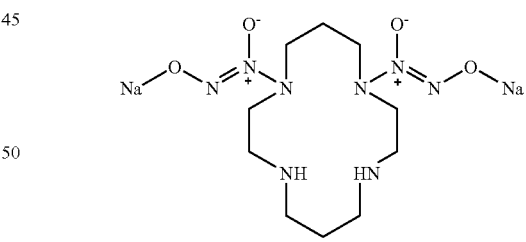

1,4,8,11-Tetraazacyclotetradecane-1,11-bisdiazeniumdiolate was prepared by reacting 1,4,8,11-tetraazacyclotetradecane (0.54 g, 2.7 mmol) in a solution of 25% NaOMe in MeOH (0.6 mL; 2.7 mmol NaOMe) and MeOH (10 mL) with 4.8 atm NO (70 psi) for 48 h. The sodium salt was precipitated by the slow addition of ether until turbidity was observed. The suspension was placed in a freezer for 24 h, after which the precipitate was isolated by vacuum filtration, washed with ether, and dried under vacuum to give a white solid (yield: 0.079 g, 8.0%); Mp: 181-182° C.; $^1$H NMR δ 1.30-1.38 (2H, m), 1.76-1.84 (2H, m), 2.62-2.78 (8H, m), 3.05-3.19 (8H, m); UV $\lambda_{max}$ 250 nm (ε=19.5 mM$^{-1}$cm$^{-1}$) (0.01 M NaOH). Anal.

Calcd. for $C_{10}H_{22}N_8O_4Na_2 \cdot \frac{3}{2}H_2O \cdot \frac{1}{2}MeOH$: C, 30.96; H, 6.68; N, 27.51. Found: C, 30.74; H, 6.77; N, 27.52.

EXAMPLE 2

This example illustrates the synthesis of 1,4,7,10-tetraazacyclododecane-1,4-bisdiazeniumdiolate.

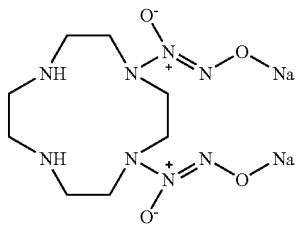

1,4,7,10-Tetraazacyclododecane-1,4-bisdiazeniumdiolate was prepared by first recrystallizing 1,4,7,10-tetraazacyclododecane from hexane:ethyl acetate and then dissolving the cyclicpolyamine (4.19 g, 0.024 mol) in a solution of 25% NaOMe in MeOH (5.6 mL; 0.024 mol NaOMe) and MeOH (25 mL) and exposing the resulting solution to 4.8 atm NO (70 psi) for 48 h. The sodium salt was precipitated by the addition of ether until the solution appeared turbid followed by cooling in a freezer for 24 h. The product was isolated by vacuum filtration, washed with ether, and dried under vacuum (yield: 0.46 g, 8.0%); Mp: 183-185° C. dec; $^1H$ NMR δ 2.60-2.70 (4H, m), 2.78 (4H, s), 3.11 (4H, s), 3.12-3.17 (4H, m); UV λ$_{max}$ 250 nm (ε=16.4 mM$^{-1}$cm$^{-1}$) (0.01 M NaOH). Anal. Calcd. for $C_8H_{18}N_8O_4Na_2 \cdot H_2O \cdot \frac{1}{3}NaOMe$: C, 26.89; H, 5.69; N, 30.10. Found: C, 26.77; H, 5.97; N, 30.18.

EXAMPLE 3

This example illustrates the NO release profiles of two compounds of the present invention.

The total moles of NO released were determined by chemiluminescence as previously described in Hrabie et al. (New Nitric Oxide Releasing Zwitterions Derived from Polyamines. *J. Org. Chem.*, 1993, 58, 1472-1476). The NO release rates for the compounds prepared in Example 1 and Example 2 were determined by UV spectrophotometry by adding a stock solution of the compound in 0.01 M NaOH to pH 7.4 phosphate buffer (0.1 M) contained in a standard UV cell to generate final solutions at concentrations in the range of 50 to 100 μM. The rate of NO release was determined by the decrease in 250-252 mm absorbance over time at 37° C. as previously described by Keefer et al. ("NONOates" (1-Substituted Diazen-1-ium-1,2-diolates) as Nitric Oxide Donors: Convenient Nitric Oxide Dosage Forms. *Methods in Enzymology*, 1996, 268, 281-293). The results of the NO release of piperazine bisdiazeniumdiolate as discussed in Hrabie et al. (*Organic Preparations and Procedures International*, 1999, 31(2), 189-192) are included as a comparative example. The results are summarized in Table 1.

TABLE 1

| Compound | Moles of NO released | Ideal moles of NO released | $t_{1/2}$ of initial phase | $t_{1/2}$ of second phase |
|---|---|---|---|---|
| piperazine bisdiazeniumdiolate (Comparative) | 4.3 | 4 | 2.3 min | 5.0 min |

TABLE 1-continued

| Compound | Moles of NO released | Ideal moles of NO released | $t_{1/2}$ of initial phase | $t_{1/2}$ of second phase |
|---|---|---|---|---|
| 1,11-bis-CYCLAM/NO (Example 1) | 3.3 | 4 | 1.7 min | 8.9 hr |
| 1,4-bis-CYCLEN/NO (Example 2) | 3.3 | 4 | 1.7 min | 8.8 hr |

The results in Table 1 illustrate that the first release of NO occurs on a minute scale for the compounds prepared in Examples 1 and 2, whereas the second release of NO occurs over many hours in comparison to piperazine bisdiazeniumdiolate.

EXAMPLE 4

This example illustrates the synthesis of 1-diazeniumdiolated-4,7,10-trisformyl-1,4,7,10-tetraazacyclododecane, sodium salt.

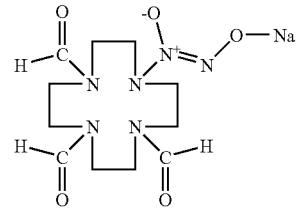

A solution of 1,4,7-trisformyl-1,4,7,10-tetraazacyclododecane (1.0 g, 3.9×10$^{-3}$ mol, prepared as described in Sisti et al., *Tetrahedron Lett.* 2000, 41, 6527-6530), in a 25% sodium methoxide solution in methanol (1.7 g, 8.0×10$^{-3}$ mol) was prepared in a vial, placed into a 250 mL glass Parr hydrogenation bottle and purged with argon. The solution was then placed under approximately 80 psi of NO gas and stirred at ambient temperature. A white precipitate formed slowly. After 24 hours, the pressure was released and the solution was purged with argon. The white precipitate was filtered, rinsed with diethyl ether and dried in vacuo resulting in a white powder. Yield: 0.158 g (11.9%). UV/Vis (0.01M aq. NaOH) {λ$_{max}$ in nm (ε in mM$^{-1}$ cm$^{-1}$)} 264 (4.0). Mp: 225-228° C. (dec.)

EXAMPLE 5

This example illustrates the synthesis of 1-diazeniumdiolated-4,7,10-tris(trifluoroacetate)-1,4,7,10-tetraazacyclododecane, sodium salt.

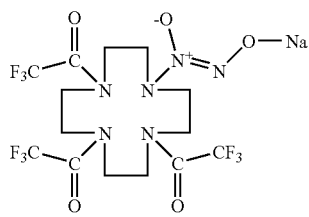

A solution of 1,4,7-tris(trifluoroacetate)-1,4,7,10-tetraazacyclododecane (0.25 g, 5.4×10$^{-4}$ mol, prepared as described in Yang et al., *Tetrahedron Lett.* 2003, 44, 2481-2483), in anhydrous dioxane (4 mL) was prepared in a vial and sodium trimethylsilanoate (0.06 g, 5.4×10⁻⁴ mol) was added. The vial was placed into a 250 mL glass Parr hydrogenation bottle and purged with argon. The solution was then placed under approximately 80 psi of NO gas and stirred at ambient temperature. After 24 hours, the pressure was released, the solution was purged with argon and the white precipitate was filtered, rinsed with diethyl ether and dried in vacuo resulting in an off-white, hygroscopic powder. Yield: 0.078 g (26.6%). UV/Vis (0.01M aq. NaOH) {$\lambda_{max}$ in nm ($\epsilon$ in mM⁻¹cm⁻¹)} 250 (2.6). Mp: 136-138° C.

EXAMPLE 6

This example illustrates the synthesis of 1,4-bis(diazeniumdiolated)-1,4,7,10-tetraazabicyclo[8.2.2]tetradecane-11,12-dione, disodium salt.

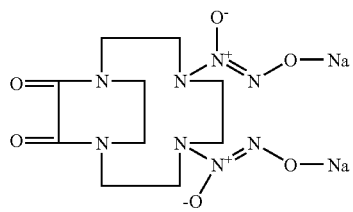

A solution of 1,4,7,10-tetraazabicyclo[8.2.2]tetradecane-11,12-dione (1.0 g, 4.4×10⁻³ mol, prepared as described in Handel et al., *J. Chem. Soc., Perkin Trans.* 1 1999, 3499-3505) in a 1:1 mixture of anhydrous methanol (20 mL) and anhydrous ether (20 mL) was prepared in a 250 mL glass Parr hydrogenation bottle, a 25% sodium methoxide solution in methanol (1.9 g, 8.8×10⁻³ mol) was added, and the reaction was purged with argon. The solution was then placed under approximately 80 psi of NO gas and stirred at ambient temperature while a white precipitate formed. After 16 hours, the pressure was released, and the solution was purged with argon and stored in a refrigerator overnight. The white precipitate was filtered, rinsed with diethyl ether, and dried in vacuo resulting in a white powder. Yield: 0.42 g (27.3%). UV/Vis (0.01M aq. NaOH) {$\lambda_{max}$ in nm ($\epsilon$ in mM⁻¹ cm⁻¹)} 248 (8.2). Mp: 195-197° C. (dec.) ¹H NMR (D₂O): 2.60-2.79 (m, 8H); 3.18 (m, 2H); 3.36-3.62 (m, 6H).

EXAMPLE 7

This example illustrates the synthesis of 1,7-diazeniumdiolated-4,10-bis(ethoxycarbonyl)-1,4,7,10-tetraazacyclododecane, disodium salt.

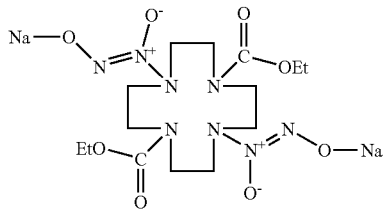

A solution of 1,7-bis(ethoxycarbonyl)-1,4,7,10-tetraazacyclododecane (0.50 g, 1.6×10⁻³ mol; prepared as described in Sherry et al., *Synthesis* 1997, 759-763) in anhydrous dioxane (3 mL) was prepared in a vial and sodium trimethylsilanoate (0.36 g, 3.3×10⁻³ mol) was added. The vial was placed into a 250 mL glass Parr hydrogenation bottle and purged with argon. The solution was then placed under approximately 80 psi of NO gas and stirred at ambient temperature for 48 hours while a white precipitate formed. The pressure was then released and the solution was purged with argon. The white precipitate was filtered, rinsed with diethyl ether and dried in vacuo resulting in a white powder. Yield: 0.30 g (39.3%). UV/Vis (0.01M aq. NaOH) {$\lambda_{max}$ in nm ($\epsilon$ in mM⁻¹ cm⁻¹)} 250 (8.9). Mp: 168-170° C.

EXAMPLE 8

This example illustrates the synthesis of 1-diazeniumdiolated-4,8,11-tris(trifluoroacetate)-1,4,8,11-tetraazacyclotetradecane, sodium salt.

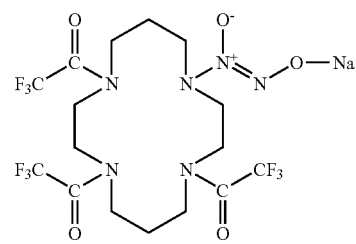

A solution of 1,4,8-tris(trifluoroacetate)-1,4,8,11-tetraazacyclotetradecane (0.60 g, 1.2×10⁻³ mol; prepared as described in Yang et al., *Tetrahedron Lett.* 2003, 44, 2481-2483) in anhydrous dioxane (3 mL) was prepared in a vial and sodium trimethylsilanoate (0.15 g, 1.3×10⁻³ mol) was added. The vial was placed into a 250 mL glass Parr hydrogenation bottle and purged with argon. The solution was then placed under approximately 80 psi of NO gas and stirred at ambient temperature. A white precipitate formed slowly and after 24 hours, the pressure was released, and the solution was purged with argon. The white precipitate was filtered, rinsed with diethyl ether, and dried in vacuo resulting in an off-white, hygroscopic powder. Yield: 0.195 g (27.9%). UV/Vis (0.01M aq. NaOH) {$\lambda_{max}$ in nm ($\epsilon$ in mM⁻¹ cm⁻¹)} 249 (3.6).

EXAMPLE 9

This example illustrates the synthesis of 1,4-bis(diazeniumdiolated)-1,5,8,12-tetraazabicyclo[10.2.2.]hexadecane-13,14-dione, disodium salt.

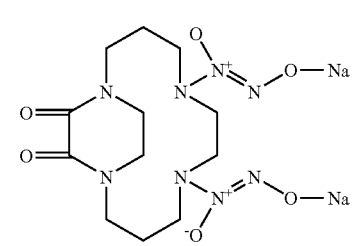

A solution of 1,5,8,12-tetraazabicyclo[10.2.2.]hexadecane-13,14-dione (0.15 g, 5.9×10⁻⁴ mol; prepared as described in Handel et al., *J. Chem. Soc., Perkin Trans.* 1 1999, 3499-3505) in anhydrous dioxane (3 mL) was prepared in a vial and sodium trimethylsilanoate (0.14 g, 1.2×10⁻³ mol) was added. The vial was placed into a 250 mL glass Parr hydrogenation bottle and purged with argon. The solution was then placed under approximately 80 psi of NO gas and stirred at ambient temperature for 48 hours as a large amount of white precipitate formed. The pressure was then released, and the solution was purged with argon. The white precipitate was filtered, rinsed with diethyl ether, and dried in vacuo resulting in a white powder. Yield: 0.245 g (100%). UV/Vis (0.01M aq. NaOH) $\{\lambda_{max}$ nm ($\epsilon$ in mM$^{-1}$ cm$^{-1}$)$\}$ 248 (12.2). Mp: 165-167° C.

EXAMPLE 10

The diazeniumdiolated compound described in Example 4 was dissolved in pH 7.4 phosphate buffer at 37° C., and the release of NO was monitored by detection of the chemiluminescence generated by treatment of the effluent gas steam with ozone. The compound had a single half-life of NO release of 2.8 min.

EXAMPLE 11

The diazeniumdiolated compound described in Example 5 was dissolved in pH 7.4 phosphate buffer at 37° C., and the release of NO was monitored by detection of the chemiluminescence generated by treatment of the effluent gas steam with ozone. The compound had a single half-life of NO release of 51.2 min.

EXAMPLE 12

The diazeniumdiolated compound described in Example 6 was dissolved in pH 7.4 phosphate buffer at 37° C., and the release of NO was monitored by detection of the chemiluminescence generated by treatment of the effluent gas steam with ozone. The compound had a biphasic release of NO resulting in two rates of release valued at 1.0 min and 41.5 min.

EXAMPLE 13

The diazeniumdiolated compound described in Example 7 was dissolved in pH 7.4 phosphate buffer at 37° C., and the release of NO was monitored by detection of the chemiluminescence generated by treatment of the effluent gas steam with ozone. The compound had a biphasic release of NO resulting in two rates of release valued at 0.36 min and 60.9 min.

EXAMPLE 14

The diazeniumdiolated compound described in Example 9 was dissolved in pH 7.4 phosphate buffer at 37° C., and the release of NO was monitored by detection of the chemiluminescence generated by treatment of the effluent gas steam with ozone. The compound had a biphasic release of NO resulting in two rates of release valued at 1.1 min and 2.69 hours.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A compound of the formula (III):

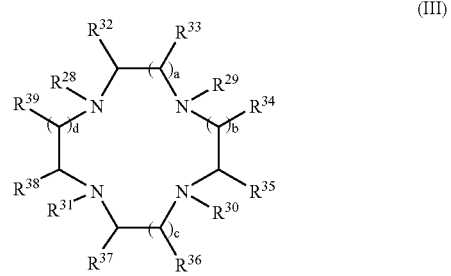

wherein at least two of $R^{28}$, $R^{29}$, $R^{30}$, and $R^{31}$ are $N_2O_2M$, wherein each $N_2O_2M$ moiety is bonded through the $N^1$ nitrogen on the $N_2O_2M$ moiety, and the remaining $R^n$ substituent(s) that are not $N_2O_2M$ can be the same or different and are independently selected from the group consisting of hydrogen, an unsubstituted or substituted $C_{1-12}$ straight chain alkyl, an unsubstituted or substituted $C_{3-12}$ branched chain alkyl, an unsubstituted or substituted $C_{3-12}$ straight chain alkenyl, an unsubstituted or substituted $C_{3-12}$ branched chain alkenyl, an unsubstituted or substituted aralkyl, an unsubstituted or substituted aryl, an unsubstituted or substituted acyl, an unsubstituted or substituted alkoxycarbonyl, an unsubstituted or substituted aryloxycarbonyl, carboxamido, and a cyclic polyamine compound comprising 3 to 6 amino groups that is bound through either a carbon or nitrogen atom in the backbone of the compound;

$R^{32}$-$R^{39}$ can be the same or different and are independently selected from the group consisting of hydrogen, an unsubstituted or substituted $C_{1-12}$ straight chain alkyl, an unsubstituted or substituted $C_{3-12}$ branched chain alkyl, an unsubstituted or substituted $C_{2-12}$ straight chain alkenyl, an unsubstituted or substituted $C_{3-12}$ branched chain alkenyl, an unsubstituted or substituted alkoxy, an unsubstituted or substituted aralkyl, an unsubstituted or substituted aryl, an unsubstituted or substituted heteroaryl, an unsubstituted or substituted arylamino, an unsubstituted or substituted alkylamino, carboxyalkylamino, carboxydialkylamino, an unsubstituted or substituted acetoxy, an unsubstituted or substituted carboxyalkyl, an unsubstituted or substituted alkylcarbonyl, an unsubstituted or substituted alkylthio, an unsubstituted or substituted alkyloxy, carboxamido, an unsubstituted or substituted alkylcarboxamido, an unsubstituted or substituted dialkylcarboxamido, an unsubstituted or substituted phenoxy, an unsubstituted or substituted benzyloxy, phenylcarbonyl, benzylcarbonyl, silyl, and a cyclic polyamine compound comprising 3 to 6 amino groups that is bound through either a carbon or nitrogen atom in the backbone of the compound;

each M is the same or different and is a pharmaceutically acceptable cation; and a-d are integers independently from 1 to 3.

2. A compound of the formula (IIIa):

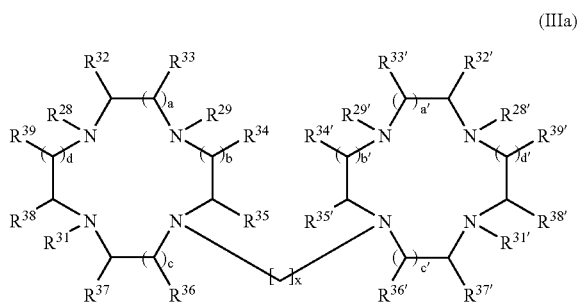

(IIIa)

wherein at least two of $R^1$, $R^2$, and $R^4$ and optionally at least one of $R^{1'}$, $R^{2'}$ and $R^{4'}$ are $N_2O_2M$, wherein each $N_2O_2M$ moiety is bonded through the $N^1$ nitrogen on the $N_2O_2M$ moiety, and the remaining $R''$ substituent(s) that are not $N_2O_2M$ can be the same or different and are independently selected from the group consisting of hydrogen, an unsubstituted or substituted $C_{1-12}$ straight chain alkyl, an unsubstituted or substituted $C_{3-12}$ branched chain alkyl, an unsubstituted or substituted $C_{3-12}$ straight chain alkenyl, an unsubstituted or substituted $C_{3-12}$ branched chain alkenyl, an unsubstituted or substituted aralkyl, an unsubstituted or substituted aryl, an unsubstituted or substituted acyl, an unsubstituted or substituted alkoxycarbonyl, an unsubstituted or substituted aryloxycarbonyl, and carboxamido;

$R^5$-$R^{12}$ and $R^{5'}$-$R^{12'}$ can be the same or different and are independently selected from the group consisting of hydrogen, an unsubstituted or substituted $C_{1-12}$ straight chain alkyl, an unsubstituted or substituted $C_{3-12}$ branched chain alkyl, an unsubstituted or substituted $C_{2-12}$ straight chain alkenyl, an unsubstituted or substituted $C_{3-12}$ branched chain alkenyl, an unsubstituted or substituted alkoxy, an unsubstituted or substituted aralkyl, an unsubstituted or substituted aryl, an unsubstituted or substituted heteroaryl, an unsubstituted or substituted arylamino, an unsubstituted or substituted alkylamino, carboxyalkylamino, carboxydialkylamino, an unsubstituted or substituted acetoxy, an unsubstituted or substituted carboxyalkyl, an unsubstituted or substituted alkylcarbonyl, an unsubstituted or substituted alkylthio, an unsubstituted or substituted alkyloxy, carboxamido, an unsubstituted or substituted alkylcarboxamido, an unsubstituted or substituted dialkylcarboxamido, an unsubstituted or substituted phenoxy, an unsubstituted or substituted benzyloxy, phenylcarbonyl, benzylcarbonyl, and silyl;

each M is the same or different and is a pharmaceutically acceptable cation;

a-d and a'-d' are integers independently from 1 to 3; and x is an integer from 1 to 6.

3. The compound of claim 1, wherein each substituent that is not $N_2O_2M$ is optionally substituted each with 1 to 20 substituents independently selected from the group consisting of alkyl, arylalkyl, alkoxy, aryloxy, arylalkyloxy, acyl, acyloxy, carboxyl, alkoxycarbonyl, aryloxycarbonyl, aralkyloxycarbonyl, carboxamido, arylamino, diarylamino, aralkylamino, amino, alkylamino, dialkylamino, formyl, alkylthio, arylthio, arylalkylthio, aryl, heteroaryl, pyrrolyl, furanyl, thiazolyl, pyrazolyl, acridinyl, anthracenyl, benzyl, benzofuranyl, benzothiophenyl, benzoxazolyl, benzopyrazolyl, benzothiazolyl, carbazolyl, chlorophyllyl, cinnolinyl, fUranyl, imidazolyl, indolyl, isobenzofuranyl, isoindolyl, isoxazolyl, isothiazolyl, isoquinolinyl, naphthalenyl, oxazolyl, phenanthrenyl, phenanthridinyl, phenothiazinyl, phenoxazinyl, phthalimidyl, phthalazinyl, phthalocyaninyl, porphinyl, pteridinyl, purinyl, pyrazinyl, pyrazolyl, pyridazinyl, pyridinyl, pyrimidinyl, pyrrocolinyl, pyrrolyl, quinolizinium ion, quinolinyl, quinoxalinyl, quinazolinyl, sydnonyl, tetrazolyl, thiazolyl, thiophenyl, thyroxinyl, triazinyl, triazolyl, pyridinyl, or pyrimidinyl, silyl, trialkylsilyl, silyloxy, sulfonyl, sulfinyl, sulfenyl, sulfonato, phosphato, phosphinoxy, trialkylammonium, heterocyclics such as tetrahydrofuranyl, tetrahydropyranyl, piperidinyl, pyrrolidinyl and morpholinol, halo, cyano, nitro, hydroxy, mercapto, cycloalkyl, glycosyl and diazeniumdiolato.

4. The compound of claim 1, wherein $R^{32}$-$R^{39}$ are each hydrogen.

5. The compound of claim 1, wherein the compound is bound to a polymer through a carbon substituent on the compound.

6. The compound of claim 5, wherein the polymer is a biopolymer.

7. A substrate comprising a compound of claim 1 wherein the substrate is a biocompatible material selected from the group consisting of metal, glass, ceramic, plastic, and rubber.

8. The substrate of claim 7, wherein the substrate is a stent.

9. The substrate of claim 7, wherein the compound is bound to the substrate.

10. The substrate of claim 9, wherein the substrate is a stent.

11. The substrate of claim 7, wherein the compound is coated on the substrate.

12. The substrate of claim 11, wherein the substrate is a stent.

13. The compound of claim 1, having the following structure:

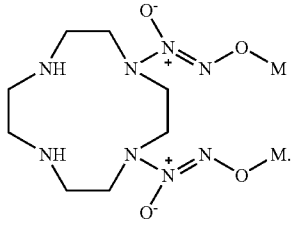

14. The compound of claim 1, having the following structure:

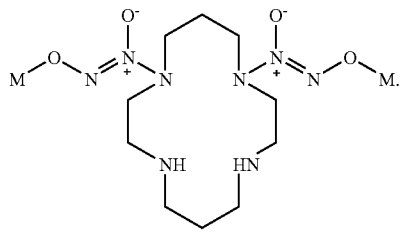

15. A pharmaceutical composition comprising a pharmaceutically acceptable carrier and at least one compound of claim 1.

16. A method of preparing the compound of formula (III) of claim 1 comprising:
(a) providing a cyclic tetraamine,
(b) selectively protecting one or more aza groups with at least one protecting group,
(c) exposing the protected cyclic tetraamine to nitrogen oxide gas in the presence of a base, and
(d) obtaining the compound of formula (III).

17. The method of claim 16, wherein the base is a metal alkoxide of the formula MOR, wherein M is a cation and R is an unsubstituted or substituted $C_{1-12}$ straight chain alkyl, an unsubstituted or substituted $C_{3-12}$ branched chain alkyl, a phenyl, naphthyl, or $C_{1-12}$ trialkylsilyl.

* * * * *